United States Patent [19]

Bier et al.

[11]  4,288,607
[45]  Sep. 8, 1981

[54] BIS-CARBALKOXY COMPOUNDS AND THEIR PREPARATION

[75] Inventors: Gerhard Bier, Troisdorf; Dagmar Kottek, Sieburg; Egon N. Petersen, Neukirchen-Seelscheid; Hermann Richtzenhain, Much-Schwellenbach; Norbert Vollkommer, Troisdorf, all of Fed. Rep. of Germany

[73] Assignee: Dynamit Nobel Aktiengesellschaft, Troisdorf, Fed. Rep. of Germany

[21] Appl. No.: 19,944

[22] Filed: Mar. 12, 1979

Related U.S. Application Data

[62] Division of Ser. No. 733,820, Oct. 19, 1976, Pat. No. 4,152,511.

[30] Foreign Application Priority Data

Oct. 25, 1975 [DE] Fed. Rep. of Germany ....... 2547802
Mar. 26, 1976 [DE] Fed. Rep. of Germany ....... 2612840
Mar. 26, 1976 [DE] Fed. Rep. of Germany ....... 2612841
Mar. 26, 1976 [DE] Fed. Rep. of Germany ....... 2612842
Jul. 23, 1976 [DE] Fed. Rep. of Germany ....... 2633096

[51] Int. Cl.³ ................. C07C 147/107; C08C 63/18
[52] U.S. Cl. ......................... 560/11; 560/57; 560/64; 560/65; 528/173; 528/191; 528/192; 528/193; 528/194; 528/209; 260/40 R; 260/45.7 R; 260/45.75 R
[58] Field of Search ............ 560/11, 57, 64, 65

[56] References Cited

U.S. PATENT DOCUMENTS

| | | | |
|---|---|---|---|
| 2,970,168 | 1/1961 | Horn et al. | 560/11 |
| 3,004,955 | 10/1961 | Horn | 560/11 |
| 3,032,534 | 5/1962 | Horn | 560/11 |
| 3,630,715 | 12/1971 | Guttag | 560/57 |
| 4,148,915 | 4/1979 | Thuillier et al. | 560/11 |
| 4,152,511 | 5/1979 | Bier et al. | 528/190 |

Primary Examiner—Hosea E. Taylor
Assistant Examiner—Amelia B. Yarbrough
Attorney, Agent, or Firm—Sprung, Felfe, Horn, Lynch & Kramer

[57] ABSTRACT

The invention relates to halogenous polyesters with the recurrent general formula

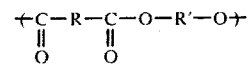

in which at least part of the R's, e.g. 1 to 100 mole-%, preferably 100 mole-%, or 2 to 10 mole-%, are of the general formulas

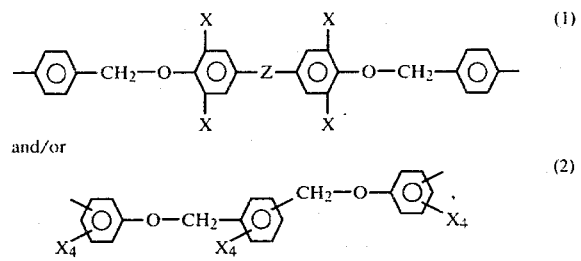

and 0 to 99 mole-%, preferably 0 or 90 to 98 mole-%, of the R's correspond to a phenylene radical and/or a naphthylene radical and/or an alkylene radical of 3 to 10 carbon atoms and/or a cycloalkylene radical, and the R's represent an organic moiety which is contained in bivalent saturated alcohols and corresponds to a branched or unbranched saturated alkylene radical of 2 to 10 carbon atoms and/or to a cycloalkylene radical and/or which is derived from an alkyleneterephthalate containing hydroxyl groups, preferably an oligomeric ethyleneterephthalate and/or an oligomeric propyleneterephthalate and/or an oligomeric butyleneterephthalate, wherein Z represents the groups

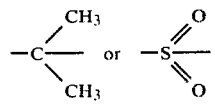

and X represents hydrogen, bromine or chlorine, wherein at least some of the X's are bromine or chlorine, and in which polyesters, in some cases, a portion of the R's are residues of unsaturated dicarboxylic acid derivatives which, together with ethylenically unsaturated comonomers, preferably styrene, are capable of forming peroxide-curable unsaturated polyester resin (UP resin) solutions, and their preparation as well as their use as fire-retardant molding compositions or articles, and also dicarboxylic acid esters some of which can be used in the preparation of the polyesters as well as the preparation of these dicarboxylic acid esters. Preferably the xylene nucleus in (2) is substituted by $Br_{4.0\ to\ 2.8}$ and $Cl_{0\ to\ 1.2}$.

6 Claims, No Drawings

BIS-CARBALKOXY COMPOUNDS AND THEIR PREPARATION

This is a division, of application Ser. No. 733,720, filed Oct. 19, 1976, now U.S. Pat. No. 4,152,511, issued 5-1-79.

The abstract is incorporated herein by reference.

One aspect of the invention relates to unsaturated polyesters.

The unsaturated polyesters are derived as regards the alcohol component from known diols or diol mixtures, preferably ethylene glycol and neopentyl glycol, and, as regards the acid component, either from unsaturated dicarboxylic acids such as maleic acid or fumaric acid, or from unsaturated dicarboxylic acid components. The new unsaturated polyesters contain recurrent units of the following formulas:

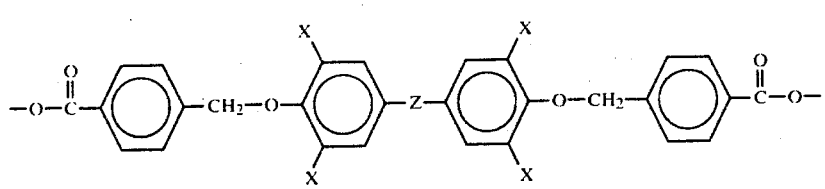

(1b)

and/or

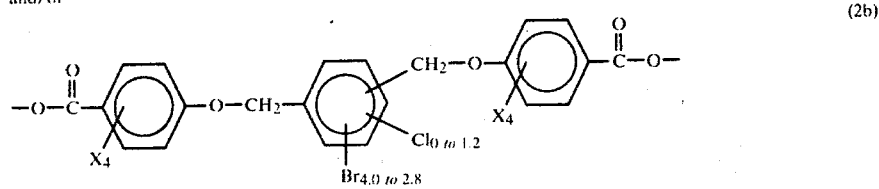

(2b)

in which X represents hydrogen, chlorine or bromine and Z represents

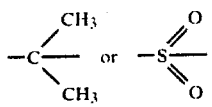

The central xylylene radical in structural formula 2b can be both meta- and para-substituted. The new unsaturated polyesters contain moieties of the structural elements of formula 1b and/or 2b in amounts of 2 to 100 mole-%, preferably 5 to 80 mole-%, with respect to the total amount of the unsaturated dicarboxylic acid components used.

Unsaturated polyesters which are derived, as regards the acid components, from unsaturated and saturated dicarboxylic acids or dicarboxylic acid mixtures, and, as regards the alcohol components, from polyvalent alcohols, are known. Their molecular weights usually range from about 1000 to 4000.

Maleic acid or its anhydride or fumaric acid are used preferentially as unsaturated dicarboxylic acids. Aliphatic or cycloaliphatic or aromatic dicarboxylic acids can be used individually or in mixture as saturated dicarboxylic acids. Mononuclear aromatic dicarboxylic acids such as orthophthalic acid or its anhydride and/or isophthalic acid and/or terephthalic acid or terephthalic acid dialkyl esters are used preferentially, as well as adipic acid from the series of the aliphatic dicarboxylic acids, and tetrahydrophthalic acid, endomethylenetetrahydrophthalic acid or hexachlorendomethylenetetrahydrophthalic acid from the series of the cycloaliphatic dicarboxylic acids.

The polyvalent alcohols involved are mainly ethylene glycol, diethylene glycol, neopentyl glycol, propanediol-1,2, butanediol-1,3 and butanediol-1,4, as well as mixtures of the latter diols.

The UP resins are used in the form of their solutions in a monomer, preferably styrene, which is copolymerizable with the maleinate or fumarate double bonds, preferably as casting resins for the production of cast articles. After the addition of radical forming agents, the UP resin solution, containing fillers or strengthening materials if desired, are shaped and hardened and, in some cases, cured. The radical formers are, for example, peroxides, preferably dibenzoyl peroxide alone, in the form of a 50% paste for example, or in combination with tertiary amines as accelerators.

An important requirement for certain applications of UP resins is resistance to hydrolysis in the presence of alkaline or acid media, or flame-resistance.

UP resins described as resistant to hydrolysis have previously been disclosed. It has been found that, by the use of those polyvalent alcohols as condensation components which give rise to the formation of sterically hindered or shielded ester groups, such as neopentyl glycol, UP resins of greater resistance to hydrolysis can be obtained than by the use of ethylene glycol or butanediol. Also, the use of isophthalic acid instead of other saturated dicarboxylic acids such as terephthalic acid or orthophthalic acid makes possible the synthesis of UP resins having improved hydrolysis resistance in comparison to standard formulations using ethylene glycol, phthalic acid anhydride and maleic acid anhydride. Furthermore, by the use of fumaric acid as the unsaturated dicarboxylic acid, or by the use of maleic acid (anhydride) with subsequent isomerization of the maleic acid structures to fumaric acid ester structures, not only is the thermal stability of shape but also the hydrolysis resistance of the UP resins hardened with styrene improved in comparison to standard UP resin formulations.

Another method of preparing UP resins more resistant to hydrolysis is pointed out by German Pat. No. 1,126,609 and by German "Offenlegunsschrift" No. 2,301,159; ethers of ethylene glycol or diethylene glycol with chlorinated biphenyl substances are used as the diol component, such as for example the bis-(β-hydroxyethoxy)-octachlorobiphenyl or Structural Formula 3, or the bis-tetrachlorophenoxyethoxyethanol of Structural Formula 4.

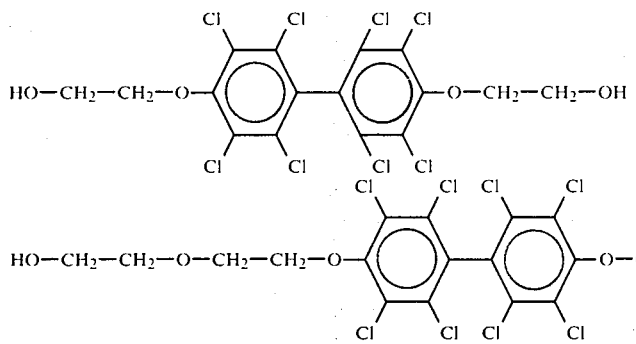

(3)

(4)

The UP resins obtainable therefrom have, as shown by our own comparative testing, greater hydrolysis resistance than standard UP resins, but they have no more than mediocre thermal stability of shape.

The present invention is addressed to the problem of creating unsaturated polyesters whose hardened products have an improved hydrolysis resistance in comparison to known resin formulations, combined with high thermal stability of shape. This problem is solved by the invention.

The subject matter of the invention is a method of preparing hydrolysis-resistant unsaturated polyesters by the polycondensation of:

(a) neopentylglycol and/or ethyleneglycol and/or diethyleneglycol and/or propanediol-1,2 and/or butanediol-1,3 and/or butanediol-1,4 and/or 1,4-bis-(hydroxymethyl)-cyclohexane and/or tetrachloro-m-xylyleneglycol and/or tetrachloro-p-xylyleneglycol and/or tetrabromo-m-xylyleneglycol and/or tetrabromo-p-xylyleneglycol with (b) a saturated dicarboxylic acid component or its polyester-forming derivatives and (c) Fumaric acid and/or maleic acid and/or maleic acid anhydride, which is characterized in that, as the dicarboxylic acid component (b), one uses, in addition to or instead of another saturated dicarboxylic acid component, the bisesters of the structural formulas 1a nd/or 2a:

UP resins formerly known as hydrolysis-resistant. An additional, unexpected advantageous property is the improved thermal stability of shape of the articles obtainable by hardening with styrene. The Martens thermal stability of shape ranges around 100° to 120° C., and hence is 10° to 30° C. higher than that of the commercially available UP resins of high thermal shape stability ranging around 90° C.

Another advantage of the UP resins containing bromine and/or chlorine in accordance with the invention lies in their fire retardancy, so that certain resin formulations containing no additives such as phosphorus or antimony trioxide achieve the classification VO in UL Test 94, and other resin formulations of the invention can be made self-extinguishing by the addition of small amounts of synergistic substances.

Additional subject matter of the invention, therefore, is flameproof UP resins in whose preparation the halogeneous compounds of Formulas 1a and/or 2a are used or incorporated as saturated dicarboxylic acid components, and flameproof UP resins which contain recurrent units of the halogenous compounds of Formulas 1b and/or 2b, and flameproof products made therefrom.

Additional subject matter of the invention is the use of the unsaturated polyesters prepared by the method of the invention in solution with copolymerizable monomers for the production of hydrolysis resistant articles of high thermal stability of shape, and also, in the case of the use of the brominous and/or chlorinated UP resins

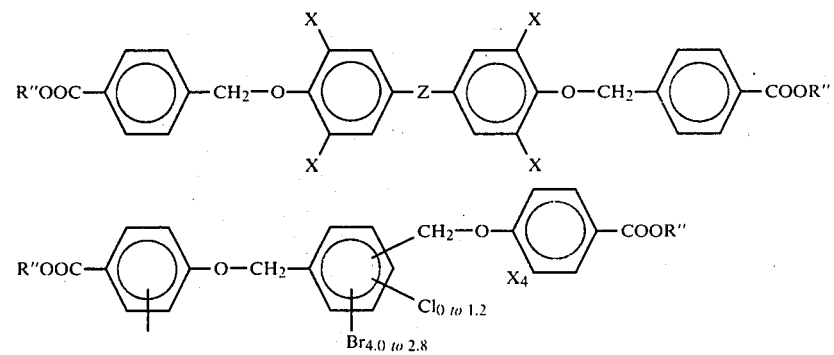

(1a)

(2a)

wherein X has the meanings given, and wherein the central xylylene moiety of Formula 2a can be both metasubstituted and para-substituted, in amounts of 2 to 100 mole-%, preferably 5 to 80 mole-%, with respect to the sum of the saturated dicarboxylic acid components. R' has the meaning given below for formulas A3 and A4. The R' 's can be alike or different.

The UP resins of the invention have a resistance to hydrolysis which is considerably better than that of the in accordance with the invention, with the incorporation in some cases of synergistic additives, their use in the preparation of flameproof or, in some cases, self-extinguishing articles. Such articles contain about 5 to 25 wt.-%, esepcially 8 to 18 wt.-%, of organically bound bromine or about 10 to 30 wt.-% of organically bound chlorine, as the case may be.

The unsaturated dicarboxylic acid component is used in amounts of 30 to 80 mole-%, preferably 40 to 70 mole-%, with respect to the total amount of dicarboxylic acid component used. The polyvalent alcohols used for the polyesters of the invention are the diols commonly used in the preparation of UP resins, such as for example ethylene glycol, diethylene glycol, propanediol-1,2, butanediol-1,4, cyclohexanedimethanol, meta- or para-xylyleneglycol, tetrachloro-m- or -p-xylyleneglycol, and neopentyl glycol. For the production of UP resins of good hydrolysis resistance, neopentyl glycol is preferred, although it has proven to be an advantage of the use of the bisesters of Structures 1a or 2a in accorance with the invention that, even with the use of concomitant use of ethylene glycol (and even of orthophthalic acid, i.e., virtually setting forth from standard formulations), it is possible to achieve hydrolysis-resistant resin formulations.

The saturated dicarboxylic acid component used in the preparation of the unsaturated polyesters of the invention are either the previously never used bis-esters of structural formulas 1a and/or 2a, by themselves or together with the dicarboxylic acids known to be used for the production of UP resins, in the form of anhydrides or other polyesters-forming derivatives, examples being adipic acid, orthophthalic acid or its anhydride, tetrahydrophthalic acid, endomethylenetetrahydrophthalic acid, tetrachlorophthalic acid, hexachlorendomethylenetetrahyrophthalic acid, isophthalic acid, terephthalic acid or its dialkyl esters, or mixtures of the individual components. Isophthalic acid and/or terephthalic acid, the latter mainly in the form of a dimethyl ester, are used preferentially in addition to the bis-esters of structural formulas 1a and/or 2a of the invention. Isophthalic acid is known as a component of hydrolysis-resistant Up resins, but the resistance to hydrolysis can be substantially further improved by the partial or complete substitution of the bis-esters of the invention for the isophthalic acid, as comparative testing has shown.

The diols and the total dicarboxylic acid component can be used in a molar ratio of 1:1; if desired, the dicarboxylic acid component or the total amount of diol component can be present in a slight excess, e.g. 20 mol. % excess.

Although generally speaking, the copolymerization of isophthalic acid yields UP resins of definitely better hydrolysis resistance than an otherwise identical resin formulation using terephthalic acid, resin formulations of the invention which contain, instead of isophthalic acid, the same amount of copolymerized terephthalic acid in addition to the bis-esters of strucutral formulas 1a or 2a have virtually the same resistance to hydrolysis in the present case. For example, a UP resin formulation using one mole of neopentyl glycol, 0.2 mole of tetrachloro-m-xylylenebis-(4-carbomethoxyphenyl) ether (Structural Formula 2c with X=Cl N=CH and R=methyl, meta bonding), 0.2 mole of terephthalic acid dimethyl ester and 0.6 mole of fumaric acid, and one using one mole of neopentyl glycol, 0.2 mole of tetrachloro-m-xylylene-bis-(4-carbomethoxyphenyl) ether, 0.2 mole if isophthalic acid and 0.6 mole of fumaric acid, when dissolved in 40 weight-parts of styrene and hardened, have the same resistance to aqueous alkali solutions or aqueous mineral acid solutions.

It is known to use, for the manufacture of fire-retardant or self-extinguishing UP resins or UP resin castings, condensation components in the form of chlorinated or brominated dicarboxylic acids or diols, such as for example tetrachlorophthalic acid, hexachlorendomethylenetetrahydrophthalic acid, tetrabromophthalic acid or dibromobutenediol, as well as dibromoneopentylglycol. To reduce flammability, these compounds have to be copolymerized in amounts which cause the chlorine content or bromine content of the end product (UP resin solution in styrene or hardened article) to increase to more than 20 wt.-% and 10 wt.-%, respectively, if the desired effect is to be achieved without additional synergistic flameproofing agents such as antimony trioxide (which in many applications cause an undesirable opacity in the castings). If self-extinguishing articles are to be produced under the above-specified conditions, their chlorine content would have to be around 30 wt.-% or their bromine content around 17%. In order to incorporate such high percentages of halogen into the UP resins by means of the said dicarboxylic acids, they have to be used in such amounts that embrittlement is observed, i.e., impairments of impact strength and elongation.

If the bromine content is introduced by means of the above-mentioned brominous diols, disadvantages must be expected on account of the comparatively low stability of the aliphatic carbon-bromine bond; the UP resins tend even during preparation to assume a brownish-red discoloration, and to cross-link spontaneously in the polycondensation stage.

On the other hand, by the use of the bromine-substituted, especially the tetrabromine-substituted bisesters of structural formula 1a and/or 2a, it is easy to introduce those halogen contents which are necessary for the achievement of self-extinguishing properties in the UP resins, resin solutions or hardened articles, without inducing undesirable discoloration much less cross-linking of the mixtures under preparation. Surprisingly in this case, no embrittlement occurs, and instead, as the thermal stability of shape of the UP resins or of the castings obtainable therefrom increases due to the copolymerization of increasing amounts of bis-esters of Structural Formulas 1a nd/or 2a, it is accompanied by a slightly increasing impact strength in the castings.

The UP resins are prepared preferably by the process of fusion polycondensation, although the described polyesters can also be prepared by polycondensation in solution or by azeotropic polycondensation. The following method can be followed in the preparation of the resins:

The dicarboxylic acid esters of Structural Formulas 1a or 2a of the invention are desirably first transesterified with the diols to be used, and after transesterification they are polymierzed with the rest of the acid components. If in addition to the dicarboxylic acid esters 1a l or 2a still other saturated dicarboxylic acids are used in the form of their dialkyl esters, such as terephthalic acid dimethyl ester for example, the latter can be transesterified together with the bis-esters 1a or 2a. The transesterification is performed in a known manner in the temperature range from 140° to 210° C., preferably 150° to 200° C., with the use of known transesterification catalysts such as lead oxide, zinc acetate, manganese acetate or titanic ester. Tetraalkyltitanates are used preferentially for the transesterification. After the transesterification has been performed and the rest of the dicarboxylic acid components, especially maleic acid, preferably in anhydride form, and/or fumaric acid, have been added, the polycondensation is carried out by a step-wise increase of temperature to a maximum of 240° C., preferably 200° to 220° C., until the desired molecular weight is achieved. If saturated free dicarboxylic acids are used as reactants, such as isophthalic acid for example, it has been found desirable, after the transesterification has been performed, first to add and copolymerize the saturated dicarboxylic acids and to add the unsaturated dicarboxylic acids as the final reactants. This order of procedure presents advantages, especially when isophthalic acid nd fumaric acid are both used; UP resins are obtained having lesser percentages insoluble in styrene, and the thermally more sensitive unsaturated dicarboxylic acids are not exposed for too long to the high condensation temperature.

To accelerate the polycondensation, it is desirable to add esterification catalysts in amounts between 0.02 and 0.2 wt.-% with respect to the total amount of the resin mixture. These are tetraalkyltitanates, tetraalkylzirconates, dialkyl tin oxide, and products of the reaction of same with aliphatic carboxylic acids (Harada complex compounds). It is preferably to use the titanate of 2-ethylhexanediol-1,3, the zirconate of 2-ethylhexanediol-1,3, and also sodium or potassium tetraphenyl borate.

Due to the sensitivity of the reactants to oxidation at the high condensation temperatures, especially the alcoholic components, both the transesterification and the polycondensation are performed in an inert gas atmosphere.

The UP resins prepared in accordance with the invention having molecular weights between 1000 and 6000, preferably between 2500 and 4000. The reduced specific viscosities (1 g/100 ml in phenol and tetrachloroethane 60:40 at 25° C.) are between 13 ml/g and 26 ml/g in the case of the preferred UP resins. They are used in the form of their soutions in a monomer, preferably styrene, which is copolymerizable with the maleinate or fumarate double bonds, preferably as a casting resin for the preparation of castings. After the addition of radical formers, the UP resin solution containing any fillers or reinforcing materials as well as any other known additives, and composed of 20 to 80 wt.-%, preferably 40 to 70 wt.-% UP resin plus a copolymerizable monomer to make 100%, is shaped and then hardened and, in some cases, cured, preferably at elevated temperatures ranging, for example, from about 50° to 150° C., especially at 120° to 140° C.

Peroxides, preferably dibenzoyl peroxide, alone, in the form of a 50% paste, for example, or together with tertiary amines as accelerators, are used as radical forming agents. The hardened castings made in accordance with the invention are colorless and, in most cases, transparent.

The testing of the UP resins for resistance to hydrolysis was performed by immersing the castings, hardened with styrene, in 20% aqueous caustic soda or in 25% aqueous sulfuric acid solution at 85° C. for 30 days.

In addition to any external alterations, such as crazing or roughening of the surface, the loss of bending strength as well as alterations in the weight of the castings were determined.

EXAMPLES

The invention will be further explained with the aid of the examples.

The values given in the examples of the invention as well as in the examples given for purposes of comparison, were determined on the basis of the following standards:

Bending Strength—DIN 53,452
Impact Toughness—DIN 53,453
Notch Impact Toughness—DIN 53,453
Ball Impression Hardness—DIN 53,456
Martens Temperature—DIN 53,458
ISO R75, A (thermal stability)—DIN 53,461
Combustibility—UL Standard EXAMPLE 1—Use of tetrachloro-m-xylylene-bis-(4-carbomethoxyphenyl)-ether; structural formula 2c with X=Cl, y=u and R″=methyl and meta substitution (prepared in example 52).

In a reacton flask provided with stirrer and gas feed tube, 104 g (1 mole) of neopentyl glycol and 54.4 g (0.1 mole) of tetrachloro-m-xylylene-bis-(4-carbomethoxyphenyl) ether are combined together with 0.1 g of the titanate of 2-ethylhexanediol-1,3 as transesterification catalyst, and transesterified at a temperature increasing from 170° to 200° C. (bath temperature). After the formation of methanol has ceased and the transesterification has thus been completed, 49.8 g (0.3 mole) of isophthalic acid is added and the mixture is condensed for 0.5 h at 200° C. Then 69.6 g (0.6 mole) of fumaric acid and 0.08 g of 2,4-di-tert-butylcresol is added to prevent a crosslinking reaction during the polycondensation and esterified for 0.5 h at 200° C. After the addition of 0.1 g of the zirconate of 2-ethylhexanediol-1,3 as esterification catalyst, the mixture is polycondensed for one hour at 200° C. and three hours at 220° C.

A virtually colorless UP resin is obtained having a molecular weight of 2900 as determined by gel cromatography in tetrahydrofuran (THF).

The UP resin is dissolved at the rate of 60 weight-parts in 40 weight-parts of styrene and hardened in a mold with 2 wt. % of dibenzoyl peroxide paste (50%) and 0.03 vol.-% of dimethylaniline (as a 10% solution in styrene) to form plates 4 mm thick which are cured for 4 h at 135° C.

The set resin has the following characteristics:
Bending Strength: 105.6 N/mm$^2$
Impact Strength: 6.6 KJ/m$^2$
Martens thermal stability of shape—108° C.
Thermal Stability of Shape per ISO/R 75; A:—123° C.

The castings are immersed for 30 days in 20% aqueous sodium hydroxide, lye or 25% sulfuric acid at 85° C. or in chlorobenzene at 40° C. After that the test specimens were still externally unaltered: no roughening or crazing was apparent on the surface.

(1) Exposure in sodium hydroxide:
   The weight change is +0.16%[1] and —0.23%[2], respectively.
   The bending strength decreased from 105.6 to 66.6 N/mm$^2$, a reduction of 36.8%.
(2) Exposure in sulfuric acid:
   The weight change is +0.17%[1] and +0.09%[2], respectively.
   The bending strength decreased by 7.6% to 97.5 N/mm$^2$.
(3) Exposure in chlorobenzene:
   The weight change is +2.5%[1] and +1.5%[2].
   The bending strength decreased by 20.5 % to 83.9 N/mm$_2$.

(1) Specimen rinsed with distilled water and then with acetone and air dried for 30 minutes (rinsed with acetone only in the case of exposure in chlorobenzene).
(2) Air dried for 3 days instead of 30 minutes.

EXAMPLES 2-15

Under conditions similar to those of Example 1, UP resins are prepared using various amounts of the bis-esters of Structural Formula 2c in accordance with the invention, namely tetrachloro-m-xylylene-bis-(4-carbomethoxyphenyl) ether, tetrachloro-p-xylylene-bis-(4-carbomethoxyphenyl) ether (X=Cl, Y=Cl, R''=methyl, meta and para substitution, respectively) and p-xylylene-bis-(4-carbomethoxyphenyl ether (X=hydrogen, Y=hydrogen, R=methyl, para substitution); they are hardened as in Example 1 in the form of styrene solutions, and the hydrolysis resistance of the castings is determined.

The resin formulations, the mechanical characteristics of the hardened castings and the weight changes and losses of flexural strength due to exposure to caustic soda solution are summarized in Tables 1 and 2.

COMPARATIVE EXAMPLES 1-5

Following the procedure of Example 1, a number of resin formulations which are offered as hydrolysis-resistant were prepared without the use of the bis-esters of the invention, and were hardened in the form of styrene solutions and tested for hydrolysis resistance as in the Examples of the Invention.

The resin formulations and the findings are summed up in Table 3.

TABLE 1

| Examples | | 2 | 3 | 4 | 5 | 6 | 7 | 8 |
|---|---|---|---|---|---|---|---|---|
| Resin formulation: | | | | | | | | |
| Neopentylglycol | (moles) | 1 | 1 | 1 | 1 | 1 | 1 | 1 |
| Tetrachloro-m-xylylene-bis-(4-carbomethoxyphenyl)-ether | (moles) | 0.05 | 0.15 | 0.2 | 0.25 | 0.3 | 0.3 | — |
| Tetrachloro-p-xylylene-bis-(4-carbomethoxyphenyl)-ether | (moles) | — | — | — | — | — | — | 0.2 |
| Isophthalic acid | (moles) | 0.35 | 0.3 | 0.2 | 0.2 | 0.15 | 0.1 | 0.2 |
| Fumaric acid | (moles) | 0.6 | 0.55 | 0.6 | 0.55 | 0.55 | 0.3 | 0.6 |
| Maleic acid | (moles) | — | — | — | — | — | 0.3 | — |
| Hardened casting:[8] | | | | | | | | |
| Bending strength | (N/mm$^2$) | 96.9 | 106.6 | 114.3 | 117.2 | 119.0 | 116.0 | 103.7 |
| Impact toughness | (KJ/m$^2$) | 6.9 | 7.2 | 7.4 | 8.2 | 8.6 | 9.2 | 5.9 |
| Martens temperature | (°C.) | 94 | 109 | 112 | 113 | 119 | 107 | 117 |
| After exposure in NaOH:[9] | | | | | | | | |
| Bending strength | (N/mm$^2$) | 46.6 | 86.4 | 102.0 | 105.5 | 110.2 | 90.7 | 92.1 |
| Loss of bending strength | (%) | 51 | 19.5 | 11 | 10 | 7 | 27.8 | 11.2 |
| Weight difference[1] | (%) | +0.37 | +0.07 | +0.12 | +0.10 | +0.09 | +0.05 | −0.04 |
| [2] | (%) | −0.18 | +0.04 | +0.08 | −0.01 | −0.007 | −0.26 | −0.15 |
| | | 4 | 3 | 3 | 3 | 3 | 4 | 3 |
| Footnotes | | | | | | | | |
| After exposure in chlorobenzene: | | | | | | | | |
| Bending strength | (N/mm$^2$) | 91.1 | | 103.1 | | | | |
| Loss of bending strength | (%) | 6 | | 10 | | | | |
| Weight loss[1] | (%) | +3.5 | | +3.4 | | | | |
| [2] | (%) | +2.6 | | +2.8 | | | | |

[1]See page 20, lines 21 to 25
[2]See page 20, lines 21 to 25
[3]No alteration in casting; surface entirely smooth.
[4]Surface slightly roughened, but no crazing.
[5]Surface slightly roughened, plus crazing.
[6]Casting completely destroyed
[8]60 wt.-parts of resin + 40 wt.-parts of styrene; hardening as in Example 1.
[9]30 days in 20% aqueous sodium hydroxide soda lye at 85° C.

TABLE 2

| Examples | | 9 | 10 | 11 | 12 | 13 | 14 | 15 |
|---|---|---|---|---|---|---|---|---|
| Resin Formulation: | | | | | | | | |
| Neopentyl glycol | (moles) | 1 | 1 | 1 | 0.8 | 1 | 1 | 0.5 |
| Ethylene glycol | (moles) | — | — | — | 0.2 | — | — | 0.5 |
| p-Xylylene-bis-(4-carbomethoxyphenyl)-ether | (moles) | — | — | — | — | 0.15 | 0.3 | 0.1 |
| Tetrachloro-m-xylylene-bis-(4-carbomethoxyphenyl) ether | (moles) | 0.2 | 0.18 | 0.1 | 0.1 | — | — | — |
| Orthophthalic acid | (moles) | — | — | — | — | — | — | 0.3 |
| Isophthalic acid | (moles) | — | 0.14 | 0.1 | 0.05 | 0.05 | 0.15 | — |
| Terephthalic acid | (moles) | 0.2 | 0.18 | 0.25 | 0.25 | 0.25 | — | — |
| Fumaric acid | (moles) | 0.6 | 0.5 | 0.55 | 0.6 | 0.55 | 0.55 | 0.6 |
| Hardened casting:[8] | | | | | | | | |
| Bending strength | (N/mm$^2$) | 109 | 111 | 103 | 100.7 | 101.5 | 118 | 96.4 |
| Impact strength | (KJ/m$^2$) | 6.8 | 8.9 | 7.7 | 6.5 | 8.2 | 9.1 | 6.2 |
| Martens temperature | (°C.) | 118 | 113 | 106 | 109 | 107 | 115 | 78 |
| After exposure in NaOH:[9] | | | | | | | | |
| Bending strength | (N/mm$^2$) | 98.3 | 96.0 | 91.5 | 82.0 | 93.6 | 109.8 | 52.1 |
| Loss of bending strength | (%) | 10 | 13.5 | 11 | 18 | 7.7 | 7 | 47 |
| Weight difference[1] | (%) | +0.4 | +0.38 | +0.19 | +0.7 | +0.15 | +0.2 | −0.7 |
| [2] | (%) | −0.04 | +0.09 | −0.02 | +0.17 | −0.01 | +0.06 | −1.2 |
| Remarks | | 3 | 3 | 3 | 4 | 3 | 3 | 4 |

Footnotes:
See Table 1

Comparative Example 6 (Table 3) relates to a standard UP resin. The hydrolysis resistance of the casting was so poor that it had completely disintegrated before the end of a 14-day exposure to NaOH lye.

As shown by Comparative Example 5, if the ethylene glycol is partially replaced with neopentyl glycol and the maleic acid is entirely replaced with fumaric acid, a slight improvement in resistance to hydrolysis is achieved, but again the casting was entirely destroyed at the end of its 30-day exposure to NaOH.

By the replacement of 0.1 mole of the phthalic acid with 0.1 mole of p-xylylene-bis-(4-carbomethoxyphenyl) ether in a formulation that is otherwise the same as in Comparative Example 5, the hydrolysis resistance can be substantially improved; under the same hydrolysis conditions, the loss of flexural strength is just 47% (Example 15).

EXAMPLE 16

The use of tetrabromobisphenol A-bis-(4-carbomethoxybenzyl) ether; Structural Formula B 1 with X=bromine, R"=methyl and Z=>C(CH$_3$)$_2$ In a round flask provided with a stirrer and gas introduction tube, 72.8 g (0.7 mole) of neopentyl glycol, 13.8 g (0.05 mole) of tetrachloro-m-xylylene glycol, 15.5 g (0.25 mole) of ethylene glycol, and 302.0 g (0.36 mole) of tetrabromobisphenol A-bis-(4-carbomethoxybenzyl) ether were combined and, after the addition of 0.12 g of the titanate of 2-ethylhexanediol-1,3, were transesterified at a temperature increasing from 170° C. to 200° C. After the formation of methanol had ceased, 6.64 g (0.05 mole) of isophthalic acid was added and esterified for ½ hour at 200° C. Then 69.6 g (0.6 mole) of fumaric acid and 0.08 g of 2,4-di-tert-butylcresol was added and condensed at 200° C. for half an hour. After the addition of 0.1 g of the zirconate of 2-ethylhexanediol-1,3, the mixture was polycondensed for 3½ hours at 210° C.

A UP resin was obtained having a bromine content of approximately 29% by weight, and a molecular weight of 3400 as determined by gel chromatography.

60 weight-parts of the UP resin are dissolved in 40 weight-parts of styrene to form a transparent solution, and hardened as in Example 1 to form transparent plates 4 mm thick.

The castings contain 17.4% of organically bound bromine and the UL Test shows them to be self-extinguishing without the addition of any synergistic fire-retardant additives such as antimony trioxide or phosphorus compounds; rating: 94/VO.

The castings have the following properties:
Bending strength: 118.9 N/mm$^2$
Impact strength: 7.1 KJ/m$^2$
Martens thermal stability of shape—116° C.
ISO/R 75; A thermal stability of shape—128° C.

After 30 days of immersion in 20% aqueous NaOH lye at 85° C. the casting is externally unaltered; the smooth surface contains no cracks or crazing. The weight change is +0.05%[1] and +0.02%[2], respectively. The bending strength amounts to 101.5 N/mm$^2$; the loss of bending strength is thus 14.6%.

EXAMPLE 17

The use of tetrachlorobisphenol A bis(4-carbomethoxybenzyl) ether; Structural Formula B 1 with X=chlorine and R"=methyl and Z=>C(CH$_3$)$_2$ By the procedure of Example 16, a UP resin with a molecular weight of 3300, as determined by gel chromatography, is prepared from the following reagents: 93.6 g (0.9 mole) of neopentyl glycol, 6.2 g (0.1 mole) of ethylene glycol, 198.6 g (0.3 mole) of tetrachlorobisphenol A-bis(4-carbomethoxybenzyl) ether, 16.6 g (0.1 mole) of isophthalic acid and 69.6 g (0.6 mole) of fumaric acid; 60 weight-parts of this resin are dissolved in 40 weight-parts of styrene, and the solution is hardened as in Example 1 to form plates 4 mm thick having the following characteristics:

Bending strength: 108.9 N/mm$^2$
Impact strength: 7.9 KJ/m$^2$
Thermal stability of shape:
  Martens: 118° C.
  ISO/R 75; A 131° C.

After 30 days of immersion in 20% aqueous NaOH lye at 85° C. the casting is externally unaltered: smooth surface, no crazing. The weight change is +0.03%[1] and +0.008%[2]. The bending strength has thus diminished but slightly to 102.3 N/mm$^2$, or 6%.

TABLE 3

| Comparative Examples | | 1 | 2 | 3 | 4 | 5 | 6 |
|---|---|---|---|---|---|---|---|
| Resin Formulation: | | | | | | | |
| Neopentyl glycol | (moles) | 0.8 | 1 | 1 | — | 0.5 | — |
| Ethylene glycol | (moles) | — | — | — | — | 0.5 | 1 |
| Bis-tetrachlorophenoxy-ethoxyethanol | (moles) | 0.2 | — | — | — | — | — |
| Bisphenol A-bis(-hydroxy-ethyl ether | (moles) | — | — | — | 1 | — | — |
| Orthophthalic acid | (moles) | — | — | — | — | 0.4 | 0.4 |
| Isophthalic acid | (moles) | 0.04 | 0.45 | 0.1 | 0.1 | — | — |
| Terephthalic acid | (moles) | 0.36 | — | 0.35 | — | — | — |
| Fumaric acid | (moles) | 0.6 | 0.55 | 0.55 | 0.9 | 0.6 | — |
| Maleic acid | (moles) | — | — | — | — | — | 0.6 |
| Hardened casting:[8] | | | | | | | |
| Bending strength | (N/mm$^2$) | 99.9 | 119.7 | 107 | 98 | 84.0 | 76.0 |
| Impact strength | (KJ/m$^2$) | 6.2 | 7.6 | 6.4 | 6.0 | 7.8 | 7.0 |
| Martens temperature | (°C.) | 89 | 91 | 93 | 92 | 64 | 55.0 |
| After exposure in NaOH lye:[9] | | | | | | | |
| Bending strength | (N/mm$^2$) | 73.2 | 62.0 | 52.5 | 36.1 | 0 | 0 |
| Loss of bending strength | (%) | 26 | 48 | 51 | 63 | 100 | 100 |
| Weight difference [1] | (%) | +0.04 | −0.9 | −0.7 | +3.2 | — | — |
| [2] | (%) | −0.3 | −1.3 | −1.2 | +1.9 | — | — |
| Remarks | | 4 | 5 | 5 | 5 | 7 | 7 |

Footnotes:
see Table 1

EXAMPLE 18

Use of tetrabromo-p-xylylene-bis(4-carbomethoxyphenyl) ether; Structural Formula C2 with X=bromine y=bromine and R"=methyl.

By the procedure of Example 16 (terephthalic acid dimethyl ester is present during the transesterification phase), a UP resin is prepared from the following components: 72.8 g (0.7 mole) of neopentyl glycol, 13.8 g (0.05 mole) of tetrachloro-m-xylene glycol, 15.5 g (0.25 mole) of ethylene glycol, 130 g (0.18 mole) of tetrabromo-p-xylylene-bis(4-carbomethoxyphenyl) ether, 34.9 g (0.18 mole) of terephthalic acid dimethyl ester, 6.64 g (0.04 mole) of isophthalic acid and 69.6 g (0.6 mole) of fumaric acid; this resin has a bromine content of about 19% and a molecular weight of 3500 as determined by gel chromatography.

50 weight-parts of this resin are dissolved in 50 weight-parts of styrene and cast as in Example 1 to form transparent plates 4 mm thick, having the following characteristics:

Bending strength: 113.6 N/mm$^2$
Impact strength: 9.3 KJ/m$^2$
Thermal stability of shape:
  Martens: 108° C.
  ISO/R 75; A 121° C.

After 30 days of immersion in 20% aqueous NaOH lye at 85° C., the casting has only lost a slight amount of its surface gloss; no crazing is to be found in the surface. The weight change is +0.08%[1] and −0.03%[2]. The bending strength has diminished by 21.5% to 89.1 N/mm$^2$.

A portion of the styrene solution of the UP resin is hardened in the presence of 6 wt.-% of antimony trioxide to form a 2 mm thick plate which, with a bromine content of about 9%, is self-extinguishing in the UL Test; rating: 94/VO.

EXAMPLE 19

The use of tetrabromo-p-xylylene-bis(4-carbomethoxyphenyl) ether.

By the procedure of Example 18, a UP resin is condensed from the following components: 98.8 g (0.9 mole) of neopentyl glycol, 22.7 g (0.05 mole) of tetrabromo-m-xyleneglycol, 260 g (0.36 mole) of tetrabromo-p-xylylene-bis(4-carbomethoxyphenyl) ether, 14.9 g (0.09 mole) of isophthalic acid and 63.8 g (0.55 mole) of fumaric acid; its bromine content is about 31 wt.-%, and its molecular weight as determined by gel chromatography is 3600.

50 weight-parts of the resin are dissolved in 50 weight-parts of styrene and hardened to form transparent plates 4 mm thick having the following characteristics:

Bending strength: 119.9 N/mm$^2$
Impact strength: 9.3 KJ/m$^2$
Thermal stability of shape:
  Martens: 115° C.
  ISO/R 75; A: 130° C.

After 30 days of immersion in 20% aqueous NaOH lye at 85° C., the casting is still unaltered externally. The weight difference amounts to +0.03%[1] and +0.009%[2]. The bending strength has diminished by 9% to 108.5 N/mm$^2$.

A 2 mm plate hardened without any fire-retardant additives and containing approximately 15.5% of organically bound bromine is self-extinguishing in the UL Test. Rating: 94/V 1.

The second aspect of the invention relates to halogenous saturated linear polyester resin having recurrent units of the general formula:

$$-(CO-R-CO.O-R'-O)-$$

in which R represents an organic moiety which is contained in bivalent saturated dicarboxylic acids or their polyester-forming derivatives, of which 1 to 100 mole-%, preferably 100%, or 2 to 10 mole-%, corresponds to the general formulas:

A1: Br-substituted diphenyl with $CH_2-O$ linkers and central Z group

A2: xylylene moiety with $X_4$, $Br_{4.0 \text{ to } 3.0}$, $Cl_{0 \text{ to } 1.0}$ substituents and/or and 0 to 99 mole-%, preferably 0 or 90 to 98 mole-%, corresponds to a phenyl moiety and/or a naphthylene moiety and/or an alkylene moiety of 3 to 10 carbon atoms and/or a cycloalkylene moiety, and R' represents an organic moiety which is contained in bivalent saturated alcohols, and corresponds to a branched or unbranched saturated alkylene moiety of 2 to 10 carbon atoms and/or a cycloalkylene moiety, and/or which is derived from an oligomeric alkylene terephthalate containing hydroxyl groups, preferably an oligomeric ethyleneterephthalate and/or an oligomeric butyleneterephthalate.

$$Z \text{ is } CH_3-\underset{|}{\overset{|}{C}}-CH_3 \text{ or } O=\underset{|}{\overset{|}{S}}=O.$$

In Formula A2, the central xylylene moiety can be either ortho-substituted or meta-substituted, or also para-substituted.

Additional subject matter of the invention is fire-retardant molding compositions whose polymer component consists substantially of the new halogenous linear polyester resin. If desired, the molding compositions contain reinforcing fillers as well as conventional additives, such as pigments, mold parting agents, and the like.

The basic building blocks of Formulas A1 and A2 are derived from the bisesters and dicarboxylic acids, respectively, of the formulas

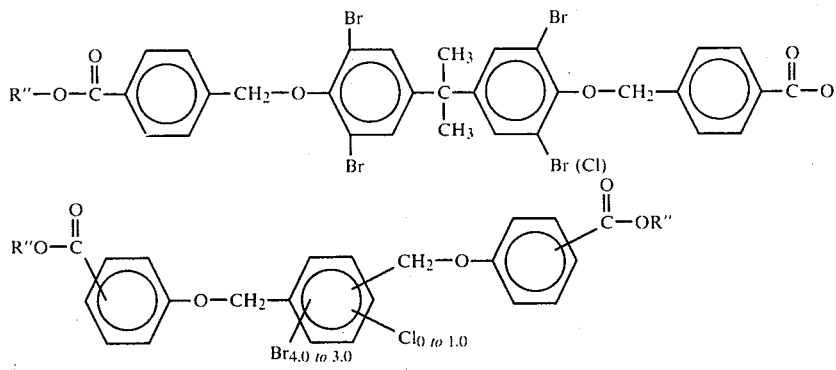

in which R″ represents hydrogen or a low alkyl moiety of 1 to 6 C-atoms such as methyl, ethyl, n-propyl, i-propyl and the like. Preferably the dimethyl esters (R″=CH₃) and diethylesters are used. The central xylylene radical of Structural Fromula 4 can have an ortho, meta or para structure. The R″'s can be alike or different. The

groups can be in the ortho, meta or para position.

In addition to the pure bromosubstitution products (Br$_{4.0}$Cl$_0$) in Structural Formulas A3 or A4, those bisesters and acids are valuable in which chlorine replaces part of the bromine—generally not more than one atom of chlorine per molecule of the bisester or acids, as the case may be, of Formulas 3 and 4, respectively (4.0Br$_{3.0}$; 1 Cl$_0$).

The small chlorine content can result from a bromine-chlorine exchange in the preparation of the bisester or in the preparation of the tetrabromoxylylenedichloride which can be produced as a preliminary step by the side-chain chlorination of tetrabromoxylene, or if, in the production of the preliminary compound, the nuclear halogen has been introduced by bromochlorination or by the use of a bromine containing chlorine.

Saturated linear polyesters which are derived with regard to the acid component from aromatic and/or aliphatic and/or cycloaliphatic dicarboxylic acids or dicarboxylic acid mixtures, and, as regards the alcohol component, from bivalent alcohols, are known. Terephthalic and isophthalic acid or their functional derivates are preferred as the aromatic dicarboxylic acids; adipic acid, azelaic acid and sebacic acid are preferred as aliphatic dicarboxylic acids, and cyclobutanedicarboxylic acid, cyclopentanedicarboxylic acid, cyclohexanedicarboxylic acid and cyclohexylenediacetic acid are preferred as cycloaliphatic acids. As bivalent alcohols, ethylene glycol, neopentyl glycol and butanediol-1,4 are preferred, as well as mixtures thereof.

Known and technologically important polyesters are, for example, polyethyleneterephthalate (PETP) and polytetramethyleneterephthalate (PTMT).

One important requirement for certain applications of the polyesters is fire-retardancy. It is general practice to render polyesters fire-retardant or incombustible by adding fire-retardant substances during their preparation or fabrication. As a rule, organic or inorganic substances of low molecular weight containing halogen or also phosphorus and nitrogen, or mixtures of such compounds with metal oxides or nonmetallic oxides which sometimes reinforce one another in their fire-retardant action, are used for this purpose. Such additives to polyesters always produce side-effects in addition to their fire-retardant action, which are undesirable because they impair the characteristic properties of the polyesters and limit their applications. Thus it is that all of the fire-retardant substances which are added to the polyester in powder form and remain in the matrix in powder form or, after the melting and mixing procedures during fabrication, when cooling takes place, are segregated again as a separate phase, act not only in the desired fire-retardant manner, but also as fillers which modify the mechanical characteristics, as a rule embrittling the polyesters and impairing their elongation at rupture and their impact strength.

Additives which are melted upon incorporation into the polyester give rise to other disadvantages: often they have either excessively high vapor pressures or excessively low decomposition temperatures at the temperatures of fabrication. In nearly all cases, the fire-retardants added have a more or less great tendency to diffuse out of the plastic or to be dissolved out of it upon exposure to fluids; this loss by diffusion not only gradually reduces the resistance of the polyesters to combustion but also, plastics rendered fire-retardant in this manner are not usable for certain purposes—for the construction of electrical apparatus, for example.

Another possibility for the preparation of fire-retardant, linear polyesters consists in the addition of condensation components containing chlorine, bromine and phosphorus in the polycondensation stage, that is, in the preparation of copolyesters using chlorinous, brominous and phosphorous basic units. The advantages of polyesters rendered fire-retardant in this manner consists in the fact that the flameproofing agent is bonded to the matrix by a homeopolar bond and thus cannot chalk out, and that the efficiency of the flameproofing agent is optimized by its extremely uniform distribution.

As a rule polyesters modified in this manner nevertheless undergo an alteration of their characteristics; especially their glass temperature is changed, as is their crystallization in the case of crystallizing products. The incorporation of flameproofing condensation components reduces not only the melting temperature but also the degree of crystallization, the rate of crystallization and the rate of formation of nuclei (corresponding to greater super-cooling or to a delay in the onset of crystallization from the melt upon cooling). The crystallization behavior of such copolyesters, especially their lower tendency to crystalize, can be advantageous, for example for the production of transparent articles by injection molding or extrusion. Thus, PETP is of limited usefulness for the production of transparent articles on account of its tendency toward crystallization. On the other hand, copolyesters on the basis of ethylene glycol and a mixture of terephthalic acid dimethyl esters and a chlorinous dicarboxylic acid ester, bis(p-carbethoxyphenoxymethyl)-2,3,5,6-tetrachlorobenzene, in a molar ratio of 1:0.2, are amorphous and transparent (H. Häberlein and H. Korbanka, Angew. Marcrom. Chemie 33 (1973), 111).

For the use of PETP as a plastic material it would be advantageous to have either a higher speed of crystallization or a very low speed of crystallization (the avoidance of any very great crystallization). In the case of PTMT a more greatly reduced speed of crystallization would be a disadvantage limiting its usefulness in most applications.

Experiments in the preparation of linear copolyesters containing the basic units of structural Formulas A1 and/or A2 in accordance with the invention have produced the unexpected result that the PETP modified in this manner has its ability to crystallize greatly impaired or inhibited, while PTMT modified in the same manner still has a similar or even greatly improved ability to crystallize in comparison with unmodified PTMT.

Whereas the incorporation of bisesters of Structural Formulas A3 and A4 in addition to dimethylterephthalate, for example, in amounts of only 5 mole-% with respect to the total amount of dicarboxylic acid, makes it possible to produce a PETP that is amorphous even after tempering, modified polytetramethyleneterephthalates containing moieties of Structural Formula A1 and/or A2 in amounts of up to 10 mole-% with respect to the total dicarboxylic acid moieties exhibit rather an advantageous crystallization characteristic in comparison to unmodified PTMT: the melting temperatures are lower by only a few degrees in comparison with plain PTMT, but the speed and degree of crystallization are surprisingly even slightly higher. A lesser supercooling of the copolyesters upon cooling from the molten state additionally indicates a higher speed of nucleation. The fire-retardant, linear polyesters of the invention, containing basic units of Structural Formulas A1 and/or A2 have, as an additional advantage, an increased resistance to hydrolysis in the presence of acids and alkalies; the reduction of molecular weight upon contact with these agents is considerably slighter in comparison with the unmodified polyesters.

An additional advantage consists in the elevated glass temperature of the polyester resins containing the fundamental units A1 and/or A2 in accordance with the invention. For example, the glass temperature of a slightly crystalline PETP of 63° C. (determined by differential thermoanalysis) is increased to 82° C. by the incorporation of 7 mole-% of fundamental units of Structural Formula 2 with respect to the total acid fundamental units.

Although experience shows that the use or concomitant use of brominous reaction components in melt condensation processes taking place in the 220° to 280° C. temperature range results in brown or reddish brown discoloration of the polycondensates, the polytetramethyleneterephthalates of the invention, modified by fundamental units of Structure 1 and/or 2, are virtually unaltered as regards color when compared with pure PTMT. This is suprising, for the polyesters PTMT and PETP modified with the chlorosubstituted rather than bromosubstituted fundamental units of Structures A1 or A2 show intensive yellow discoloration and brownish yellow discoloration, respectively, and as a rule a substantially higher thermal discoloration resistance is attributed to organic aromatic chlorine compounds than to the corresponding bromine compounds.

The synthesis of the brominous bisesters of Structural Formulas A3 and A4 are described herein.

In the preparation of the substances of Structural Formula A3, the procedure is, for example, to react tetrabromobisphenol A, together with a sufficient amount of alkali hydroxide, preferably sodium hydroxide, for the formation of phenolate, with p-chloromethylbenzoic acid alkyl ester in solution at 40° to 150° C.

Instead of p-chloromethylbenzoic acid alkyl ester, p-bromomethylbenzoic acid alkyl ester can also be used, although the chloromethyl ester is preferred for reasons of economy.

As solvents, those solvents are preferred in which sodium hydroxide as well as the bisphenols or their phenolates can be dissolved to a sufficient extent. The solvents are to have boiling points above 90° C., generally above 100° C., preferably in mixture with water. It is also possible to use solvents having a lower boiling point; in this case operation under pressure is recommendable.

Solvents of this kind are especially ethyleneglycolmonomethyl ether; also, dioxane, methylisobutylketone, methylethylketone, and the like. The amount of water in these solvents is not critical, and can to amount to as much as 65%, but preferably up to 25%, depending on the solubility of the substances to be dissolved. The hydroxides can be added to the reaction mixture in the form of aqueous solution. It is desirable to use amounts of alkali hydroxide which are equivalent to the bisphenol, since an excess results in secondary reactions with the chloromethyl or bromomethyl benzoic acid esters.

The temperature during the reaction amounts generally to from 40° to 150° C., it being desirable to maintain at the beginning a temperature suitable for the production of the phenolate, between room temperature and about 50° C. To complete the reaction, temperatures above 70° C., for example up to the boiling point of the solvent, are desirable.

Either while the reaction is still in progress or upon the cooling of the mixture, the desired products precipitate in good purity. Further refinement is possible by washing with water until the products are free of halogen, or by recrystallization from a great number of solvents.

The new acids of Formula A3, in which $R''=H$, can be prepared by hydrolysis of the esters ($R''=$low alkyl moiety).

In the production of the substances of Formula A4, a procedure can be followed which is similar to the procedure used in preparing the substances of Formula 3. The new substances can be obtained by the reaction of ortho- or meta- or para-bis(halogenmethyl)-benzenes (the halogen is preferably Cl or Br, but especially Cl), together with a sufficient amount of alkali hydroxide for the formation of phenolate, with o-, m- or p-hydroxybenzoic acid alkyl esters in solution at 40° to 150° C.

The temperatures to be applied and the other reaction conditions are the same as those described in the case of the substances of Structural Formula A3.

The new acids in accordance with Structural Formula 4, in which $R''=H$, can be prepared by hydrolysis of the esters ($R''=$low alkyl moiety).

For reasons of economy, the esters of Structural Formulas A3 and/or A4 are given preference in the synthesis of the new halogenous polyesters, since the preparation of the free acids requires an additional procedural step.

In the preparation of the polyester resins of the invention, a procedure similar to that of the known preparation of PETP and PTMT can be followed.

The dicarboxylic acid esters and dicrboxylic acids of Structural Formulas 3 or 4, as the case may be, are transesterified or esterified, respectively, either alone or in mixture with nonbrominated dicarboxylic acids or dicarboxylic acid esters, with the diols or diol mixtures, in the presence of transesterification or esterification catalysts, as the case may be, and then polycondensed by increasing the temperature, preferably with the application of a vacuum, with further transesterification or esterification and removal of the excess alcohols or of the water from the equilibrium, until the desired molecular weight is achieved.

The following are mentioned as examples of saturated dicarboxylic acids for concomitant use: terephthalic acid and/or isophthalic acid and/or naphthalenedicarboxylic acid and/or adipic acid and/or sebacic acid and/or azelaic acid and/or cyclohexanedicarboxylic acid and the like, and/or their polyester-forming derivatives such as, for example, low alkyl esters, preferably dialkyl esters, and especially dimethyl esters.

The dicarboxylic acid component to be used preferentially is dimethylterephthalate.

Suitable diol components are diols known for the production of linear saturated polyesters, either singly or in mixture. Examples are glycols of the formula HO-R-OH wherein R represents a branched or unbranched alkylene moiety or a cycloalkylene moiety of 2 to 10 carbon atoms. Specific examples of these are: ethylene glycol, propanediol-1,3, propanediol-1,2, butanediol-1,4, butanediol-1,2, butanediol-1,3, hexanediol-1,6, neopentyl glycol, 1,4-dimethylolcyclohexane, 1,3-dimethylolcyclohexane, and the like. Preferred are ethylene glycol and/or butanediol-1,4. Additional suitable diols are also, for example, oligomeric preliminary condensation products of terephthalic acid which contain hydroxyl terminal groups, preferably dimethyl esters thereof with alkylene glycols of the above-given formula. They can be used as sole diol components or they can be used together with one or more other diols, preferably butanediol-1,4 and/or ethylene glycol. Preferred oligomeric preliminary condensates are derived from terephthalic acid, preferably from its dimethyl esters and ethylene glycol and/or butanediol-1,4. Preferred are oligomeric alkylene terephthalates having a reduced specific viscosity of 0.05 to 0.5, preferably of 0.1 to 0.2.

In the preparation of the polyesters of the invention, the acid component and the diol component are best used in the molar ratio of 1:1.1 to 1:1.5, preferably 1:1.2 to 1:1.4.

In the preparation of the polyester resins of the invention, the transesterification and polycondensation catalysts can be the compounds known to be used for transesterification and polycondensation reactions, examples being zinc acetate, manganese acetate, germanium dioxide or titanic esters. The titanic esters are used preferentially, for example tetrabutyl titanate or the transesterification product between tetrabutyl titanate and 2-ethylhexanediol-1,3. It is desirable to use the catalysts in amounts of 0.01 to 0.2, preferably 0.015 to 0.05 percent by weight with respect to the total of the polycondensation components.

As a result of the sensitivity of the reactants to oxidation, especially the alcoholic components, at the high condensation temperatures, both the transesterification and the polycondensation are performed in an inert gas atmosphere or vacuum. The esterification or transesterification is generally performed at temperatures of 150° to 220° C., preferably 160° to 200° C. The subsequent polycondensation is generally performed in a vacuum in the temperature range of 200° to 250° C., preferably with the vacuum being reduced step-wise or continuously to 1 Torr or less.

The preparation of the oligomeric alkylene terephthalates can be performed as described in Patent Applications P 25 04 156.9* and P 25 04 258.4.** In this procedure, dimethylterephthalate and a diol, in a molar ratio of 1:1.1 to 1:1.5, preferably 1:1.2 to 1:1.4, and a catalyst, are continuously fed into the uppermost chamber of a heated reactor consisting of a plurality of interconnected chambers disposed vertically one above the other. The transesterification reaction is performed under normal pressures at temperatures increasing from chamber to chamber. Then, for the condensation, the excess diol is driven off in additional directly connected or separate chambers at further elevated temperature and a corresponding vacuum, until the desired degree of condensation, corresponding to reduced specific viscosities of 0.05 to 0.5, preferably of 0.1 to 0.2, is achieved. In general, the temperature at the beginning of the transesterification is 130° to 160° C. in the uppermost chamber, and increases to 180° to 210° C. in the bottom chamber of the normal pressure section. The condensation of the transesterification product is generally performed at 180° to 250° C., preferably 220° to 240° C., with the application of a vacuum. The pressure amounts generally to from 300 down to 20 Torr, preferably 250 down to 50 Torr.

*U.S. Ser. No. 653,184, filed Jan. 28, 1976 **U.S. Ser. No. 653,183, filed Jan. 28, 1976.

The substances of Structural Formula A3 and/or A4 are used preferably for the preparation of modified polyethylene terephthalates or polytetramethylene terephthalates.

In the preparation of modified polyethylene terephthalates and polytetramethylene terephthalates, the condensation components of Structural Formulas 3 and/or 4 can be added to the oligomeric preliminary condensates of DMT with ethylene glycol (OET) or of DMT with butanediol-1,4 (OBT) directly, and can be polycondensed in the mixture to the desired molecular weight. It is also possible, however, to esterify the condensation components of Structures 3 or 4 first with ethylene glycol or butanediol-1,4, if the free acids are involved, or to transesterify them if the ester derivatives are involved, and then to add the oligomeric preliminary condensates OET or OBT, and polycondense them together.

By varying the molar ratios of the dicarboxylic acid mixtures used as the dicarboxylic acid component, or by combining with a diol or diol mixture the bisesters or dicarboxylic acids of Structural Formulas 3 and/or 4, which with the invention as the sole dicarboxylic acid component, it is possible to adapt halogen-containing, saturated, linear polyester resins to the desired application with regard to their mechanical, optical, fire-retardant and other such properties.

Halogenous polyester reins having valuable properties are, for example, those in which 2 to 10 mole-% of the moiety R corresponds to the General Formulas A1 and/or 2, and 90 to 98 mole-% thereof corresponds to the terephthalic acid moiety, the moiety R' being an ethylene moiety and/or a tetramethylene moiety.

Additional halogenous polyesters of outstanding properties are those in which 100% of the moiety R corresponds to the General Formulas A1 and/or A2, and the moiety R' is derived from an oligomeric alkylene terephthalate, preferably an oligomeric ethylene terephthalate or an oligomeric tetramethylene terephthalate.

In general, the reduced specific viscosities of the halogenous polyester resins of the invention (and of this aspect of the invention) range from 0.5 to 2.5 preferably 0.8 to 1.6, measured in a 1% solution in phenol and O-dichlorobenzene in a weight-ratio of 60:40, at 25° C.

The halogen contents of the polyester resins of the invention and of this aspect of the invention range generally from 1 to 30 wt.-% and preferably from 3 to 10 wt.-%.

When the new halogenous, saturated, linear polyester resins are used as polymer components in molding compositions containing, if desired, reinforcing fillers and any desired conventional additives such as pigments, mold parting agents and the like, fire-retardant or flame-resistive molding compositions are obtained. It is desirable to add to such molding compositions synergistic substances such as antimony or boron compounds, preferably antimony trioxide. The amounts vary from 2 to 12, preferably 4 to 7, percent of the total weight of the composition.

Reinforcing fillers are, for example, glass powder, glass spheres, glass fibers and the like. Glass fibers are used preferably as reinforcing fillers, and they may be provided with a dressing, if desired, in a known manner. In general, the amounts of reinforcing filler range from 2 to 60% of the total weight of the composition.

The incorporation of additives, such as reinforcing fillers and the like, can be accomplished in a known manner, preferably by melt compounding.

The molding compositions of the invention can be worked by conventional forming methods, such as extrusion, injection molding and the like.

EXAMPLE 20

In a 500 ml two-necked flask, equipped with stirrer and a descending cooling system, the following are weighed in: 29.4 g (0.035 mole) of the bisester of Structural Formula A3 wherein R''=methyl, 187.2 g (0.965 mole) of DMT and 126 g (1.04 moles) of butanediol-1,4, plus 0.07 g of the titanate of 2-ethylhexanediol-1,3. Transesterification is performed for 4 hours at temperatures increasing from 160° to 180° C. After the formation of methanol has ceased, the temperature is increased step-by-step over a period of two hours to 250° C., and a vacuum is applied, and is increased step-wise to the optimum value (approx. 1 Torr); only one hour after the optimum vacuum has been reached, the formation of the viscous polyester can be stopped. The copolyester hardens upon cooling to an opaque, tough, virtually colorless mass with a slight yellowish tinge. The $n_{sp/c}$ is 1.2; the bromine content is 4.58%. The TGA weight losses (air; heating rate 8° C./min) amount to 1% at 336° C., 5% at 357° C., 10% at 365° C. and 20% at 375° C.

A listing of other properties is presented in Table 1.

EXAMPLE 21

By the same procedure as in Example 20, a copolyester having an $n_{sp/c}$ of 0.94 and a bromine content of 6.26% as determined by elemental analysis is prepared from the following reaction components: 42 g (0.05 mole) of bisester of Structural Formula A3 with R''=methyl, 184 g (0.95 mole) of DMT, and 126 g (1.4 moles) of butanediol-1,4, with the addition of 0.08 g of titanate of 2-ethylhexanediol-1,3. A number of additional properties are summarized in Tables 4 and 5.

EXAMPLE 22

36.1 g (0.05 mole) of bisester of Structural Formula A4 with a bromine content of 41.96% and a chlorine content of 1.63%, with R''=CH$_3$, and with para-substitution of the xylylene group and the

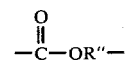

group in the para position, 184.3 g (0.95 mole) of DMT and 126 g (1.4 moles) of butanediol-1,4, plus 0.06 g of the titanate of 2-ethylhexanediol-1,3, are first transesterified for 4 hours in a polycondensation vessel at temperatures increasing from 170° to 190° C., and then polycondensed up to 250° C., under a vacuum after 225° C., to an n sp/c of 0.96.

The copolyester, which upon cooling crystallized to an opaque mass, was virtually colorless. The bromine content, determined by elemental analysis, was 6.07%; the chlorine content was 0.3%; the weight loss (TGA; heating rate 8° C./min) is 1% at 349° C., 5% at 367° C., 10% at 375° C. and 20% at 384° C. A number of additional properties are given in Tables 4 and 5.

EXAMPLE 23

From 25.3 g (0.035 mole) of the same bisester as in Example 22, 187.2 g (0.965 mole) of DMT and 126 g (1.4 moles) of butanediol-1,4, with the addition of 0.05 g of tetrabutyl titanate, a brominous copolyester is condensed by the procedure of Example 2, having an n sp/c of 1.35.

The copolyester which crystallizes upon cooling to an opaque mass is virtually colorless and is externally indistinguishable from a plain polytetramethylene terephthalate (Comparative Example 28) prepared as a comparative specimen.

The copolyester has a bromine content of 4.4% and a chlorine content of 0.2%. The TGA weight loss (air; heating rate 8° C./min) amounts to 1% at 348° C.; 5% at 368° C.; 10% at 377° C. and 20% at 386° C.

A number of additional properties are listed in Tables 4 and 5.

EXAMPLE 24

17.6 g of bisester of Structural Formula A3 with R''=CH$_3$ and 7.56 g (0.084 mole) of butanediol-1,4, plus 0.01 g of tetrabutyl titanate are weighed into a reaction vessel and transesterified for 2 hours at from 180° to 200° C. under a slow current of nitrogen. After the addition of 127.5 g of OBT (same characteristics as in Example 25), the temperature was increased step-wise to 240° C. with progressive improvement of the vacuum. After 1 hour, at 240° C. and optimum vacuum, the polycondensation is stopped.

The copolyester, with a reduced specific viscosity of 0.98, crystallizes upon cooling to an opaque mass with a slight yellow tinge. The bromine content is 4.68%.

The TGA weight losses (air atmosphere, heating rate 8° C./min) are: 1% at 337° C., 5% at 358° C., 10% at 367° C. and 20% at 380° C.

Additional characteristics are given in Table 4.

EXAMPLE 25

127.5 g of oligomeric butylene terephthalate (OBT) with a hydroxyl number of 105, an acid number of 2.7 and a reduced specific viscosity of 0.15 (corresponding to $\bar{M}_n$ of approximately 2500) and 15.25 g (0.021 mole) of the same bisester as in Example 22 are placed in a polycondensation reactor together with 0.04 g of tetrabutyl titanate, and transesterified under a slow current of nitrogen for a period of 2 hours at temperatures increasing from 200° to 225° C. The temperature is then increased step-wise to 240° C. and the vacuum is improved. After 2 hours at 240° C. and optimum vacuum, a viscous copolyester melt has formed.

The copolyester, which crystallizes to an opaque mass upon cooling, is virtually colorless and is visually undistinguishable from the plain PTMT of Comparative Example 28. The bromine content determined by elemental analysis is 4.6%, the chlorine content 0.16%. The reduced specific viscosity is 1.1. The TGA weight loss is 1% at 333° C., 5% at 364° C., 10% at 374° C. and 20% at 383° C.

Some additional characteristics are given in Table 4.

EXAMPLE 26

By the same procedure as in Example 25, out of 125.4 g of OBT with a hydroxyl number of 105, an acid number of 2.7 and a reduced specific gravity of 0.15, and 21.66 g (0.03 mole) of the same bisester as in Example 22, with the addition of 0.07 g of the titanate of 2-ethylhexanediol-1,3 as catalyst, a copolyester is prepared having a reduced specific gravity of 0.83, a bromine content of 6.1% and a chlorine content of 0.35%. The copolyester in the crystalline state is an opaque, colorless mass which is undistinguishable in appearance from the plain PTMT prepared in Comparative Example 28 as a comparative specimen.

EXAMPLE 27

43.4 g (0.06 mole) of the same bisester as in Example 22 and 43.5 g (0.48 mole) of butanediol-1,4 are weighed into a reaction vessel together with 0.05 g of the titanate of 2-ethylhexanediol-1,3 as catalyst, and transesterified for 2 hours at temperatures increasing from 180° to 200° C. under a weak current of nitrogen. After the addition of 250.8 g of OBT (having the characteristics specified in Example 25), the temperature is increased step-wise to 240° C. with progressive improvement of the vacuum. After 3 hours from the addition of the OBT, the polycodensation is terminated. The copolyester, of a reduced specific viscosity of 1.20, hardens upon cooling to an opaque, colorless mass which is undistinguishable in appearance from the plain PTMT of Comparative Example 28.

The bromine content of the polyester is 6.17%, the chlorine content 0.24%. The TGA weight loss is 1% at 338° C., 5% at 364° C., 10% at 374° C. and 20% at 382° C.

Some additional characteristics are given in Table 4.

COMPARATIVE EXAMPLE 28

Preparation of Polytetramethylene Terephthalate as a Material for Comparison.

In a two-necked flask, equipped with a stirrer, 194 g (1 mole) of DMT and 126 g (1.4 mole) of butanediol-1,4 are combined together with 0.1 g of the titanate of 2-ethylhexanediol-1,3 as catalyst, and transesterified for 4 hours in the 180° to 190° C. temperature range under a slow current of nitrogen. The temperature is raised to 225° C., a vacuum is applied, and then the temperature is further increased to 250° C. as the vacuum is increased. After 1 hour at 250° C. and optimum vacuum, the polycondensation is ended. Upon cooling, the PTMT crystallizes to an opaque, colorless mass. Reduced specific viscosity: 1.54. The TGA weight loss is 1% at 351° C., 5% at 373° C., 10% at 381° C. and 20% at 390° C. A number of additional characteristics are compared in Tables 4 and 5 with those of the brominous copolyesters of the invention.

EXAMPLE 29

50.5 g (0.07 mole) of the same bisester as in Example 22, 180.4 g (0.93 mole) of DMT and 155.0 g (2.5 moles) of ethylene glycol are weighed into a polycondensation vessel, and 0.2 g of zinc acetate is added as transesterification catalyst. Under a slow current of nitrogen, the transesterification is performed for 4 hours at temperatures increasing from 180° to 200° C.; 0.4 ml of triphenylphosphite and 0.25 g of a germanium oxide solution (10 g germanium oxide in 120 ml of solution) are added and the reaction temperature is raised step-wise to 220°, 240° and 260° C. Upon reaching 260° C. a vacuum is applied and increased step by step. After 3 h at 260° C. and optimum vacuum, the polycondensation is discontinued. The copolyester has a reduced specific viscosity of 1.06, is transparent, has a slight yellow tinge, and even after 3 days of tempering at 100° C. it is still radioamorphous. The glass temperature as determined by the DTA method is 82° C.

When compressed at 260° C. to form plates 1 mm thick, the copolyester, after 14 days of immersion at room temperature in 30% sulfuric acid, undergoes a reduction of its reduced specific viscosity to 0.92, and in 10% sulfuric acid to 0.9. The weight change after immersion in sulfuric acid under the above conditions is +0.34%, and after drying over phosphorus pentoxide it is −0.05%; after immersion in aqueous NaOH lye it is +48%, and after drying over phosphorus pentoxide it is −0.16%. Water absorption at room temperature is as follows:

After 7 days 0.44%
After 14 days 0.48%
After 28 days 0.63%

EXAMPLE 30

101.3 g (0.14 mole) of bisester of Structural Formula A4 as in Example 22, 258.4 g (1.33 moles) of DMT, 176 g (1.63 moles) of neopentyl glycol and 114 g (1.84 moles) of ethylene glycol are combined in a reaction flask as condensation components together with 0.15 g of lithium hydride as catalyst, and transesterified under a slow current of nitrogen under temperatures rising from 150° to 200° C. over a period of 1½ hours. 220.4 g (1.32 moles) of isophthalic acid and 0.9 ml of triphenyl phosphite are added, and condensation is performed for ½ hour at 200° C. and ½ hour at 220° C; then 0.6 g of a germanium oxide solution (10 g of germanium oxide in 120 ml of a mixture of ethylene glycol and triethyl amine) and the reaction temperature is increased step-wise to 270° C. At 260° C. a vacuum is applied and increased step-wise. After 3 h at 270° C. and at optimum vacuum, the polycondensation is stopped. Upon cooling, the copolyester solidifies to a transparent, yellow, amorphous mass. The reduced specific viscosity is 0.96 and the glass temperature by the DTA method is 70° C.

When pressed to form plates 1 mm thick, the copolyester, after 14 days of immersion at room temperature in 30% sulfuric acid, undergoes a reduction of its reduced specific viscosity to 0.91; in 10% aqueous NaOH lye its reduced specific viscosity drops to 0.93. The change in weight due to immersion under the aforesaid conditions in sulfuric acid is +0.23%, and, after drying over phosphorus pentoxide, −0.005%; in NaOH lye, +0.27% and, after drying over phosphorus pentoxide, −0.18%. Water absorption at room temperature:
After 7 days 0.31%
After 14 days 0.40%
After 28 days 0.75%.

COMPARATIVE EXAMPLE 31

By the procedure of Example 29, polyethylene terephthalate (PETP) having a reduced specific viscosity of 1.17 is prepared from 115.8 g (0.6 mole) of DMT and 186.2 g (3 moles) of ethylene glycol with the addition of 0.2 g of zinc acetate as transesterification catalyst plus 0.2 ml of triphenylphosphite as antioxidant. The opaque, partly crystalline material has a glass temperature (DTA method) of 63° C.

When pressed at 260° C. to form 1 mm thick plates, the reduced specific viscosity of the PETP after 14 days of immersion at room temperature in 30% sulfuric acid is diminished to 0.97, and in 10% aqueous NaOH lye it is diminished to 0.84. After immersion under the above conditions, the weight change induced by sulfuric acid is +0.37%, and, after drying over phosphorus pentoxide, +0.02%, and that induced by NaOH lye is −0.26% and, after drying over phosphorus pentoxide, −0.9%.

EXAMPLE 32

The copolyester of Example 20, with a bromine content of 4.58%, is processed together with 5 wt.-% of antimony trioxide in a double-screw extruding machine. The extruded strands are granulated and injection-molded to form test specimens measuring 1.6×12.7×128 mm for Underwriters Laboratories Test UL 94. Rating: UL 94 VO/VO (before and after 14 days at 70° C. Weight loss after 7 days at 150° was 0.14%, the material showing no alteration nor the formation of any coating during this period.

EXAMPLE 33

The copolyester of Example 21, with a bromine content of 6.26%, is made into strands together with 4 wt.-% of antimony trioxide in a dual-screw extruding machine and then granulated. Test specimens made by injection molding from the granules achieve a rating of VO/VO in the UL 94 test.

The weight loss after 7 days at 150° C. is 0.18%, the material showing no alteration nor the formation of any coating during this period of exposure to heat.

EXAMPLES 34 and 35

The copolyesters of Examples 22 and 23, with a halogen content of 6.07% bromine and 0.3% chlorine, and 4.4% bromine and 0.2% chlorine, respectively, are made into strands together with 4 and 5 wt.-% of antimony trioxide, respectively, in a dual-screw extruding machine. The strands are granulated and injection molded to make test specimens for the UL 94 test. The UL 94 rating for both specimens is VO/VO. The weight loss after 7 days at 150° C. is 0.16% for Example 34 (copolyester from Example 22) and 0.19% for Example 35 (copolyester from Example 23). Neither material shows any alteration nor any coating during this exposure to heat.

COMPARATIVE EXAMPLE 36

A mixture consisting of 86 wt.-% of PTMT (reduced specific viscosity 1.28), 9 wt.-% of commercial pentabromodiphenyl ether and 5 wt.-% of antimony trioxide is made into strands in a dual-screw extruding machine. The strands are granulated and injection molded to form test specimens for the UL 94 test. UL 94 Test Rating: VO/VO (before and after 14 days at 70° C.). Weight loss after 7 days at 150° C.: 3.4%; material has a thick, white coating.

EXAMPLE 37

By the procedure of Example 22, a brominous copolyester having a reduced specific viscosity of 0.94 was prepared from 25.3 g (0.035 mole) of bisester of Structural Formula 4:

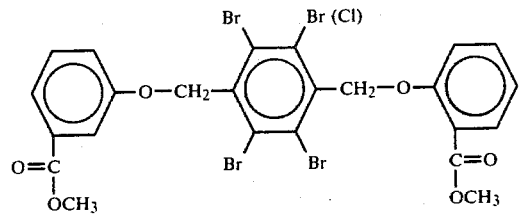

having a bromine content of 41.42% and a chlorine content of 1.80%, 187.2 g (0.965 mole) of DMT and 126 g (1.4 moles) of butanediol-1,4, with the addition of 0.05 g of tetrabutyl titanate. The transesterification and polycondensation speed are virtually the same as in Example 22 or 23.

The copolyester which crystallizes upon cooling to an opaque mass is virtually colorless and is not visually distinguishable from a plain polytetramethylene terephthalate prepared as a comparative specimen (Comparative Example 28).

The TGA weight loss is 1% at 330° C., 5% at 353° C. and 10% at 370° C. (heating rate 8° C./min, air atmosphere).

The crystallization behavior is indicated in Table 4.

EXAMPLE 38

By the procedure of Example 22 a brominous copolyester having a reduced specific viscosity of 1.13 is polycondensed from 36.1 g (0.05 mole) of the same bisester as in Example 37, 184.3 g (0.95 mole) of DMT and 126 g (1.4 moles) of butanediol-1,4, plus 0.06 g of the titanate of 2-ethylhexanediol-1,3. The transesterification and polycondensation speeds are virtually the same as in Example 22.

The copolyester which crystallizes upon cooling to an opaque mass is virtually colorless.

The TGA weight loss (heating rate 8° C./min, air atmosphere) is 1% at 330° C., 5% at 347° C. and 10% at b 358° C.

The crystallization behavior is indicated in Table 1.

TABLE 4

Melting and crystallization behavior of the linear brominous copolyesters of the invention on the basis of butanediol, DMT and the bisesters (BE) of Structural Formulas A3 and A4, compared with PTMT on the basis of DTA measurements(1).

| Polyester of Ex. No. | Dicarboxylic Acid compos. (numbers = mole-%) | Melting temp. $T_s$ (2) °C. | Crystallization temp. $T_k$ °C. (2) | Nucleation speed (supercooling $T_s-T_k$) | Degree of crystallization (area of melting peaks) cm² | Speed of crystallization (width of crystallization peaks) (3) |
|---|---|---|---|---|---|---|
| Comp. Ex. 28 PTMT | 100 DMT | 229 | 189 | 40 | 5.5 cm² | 3.5 min. |
| Ex. 20 | 96.5 DMT + 3.5 BE (3) | 223 | 183 | 40 | 5.0 cm² | 3.25 min |
| Ex. 21 | 95 DMT + 5 BE (3) | 222 | 183 | 39 | 5.5 cm² | 3.0 min |
| Ex. 23 | 96.5 DMT + 3.5 BE (4-p) | 224 | 186 | 38 | 6.0 | 3.0 min |
| Ex. 22 | 95 DMT + 5 BE (4-p) | 221 | 183 | 38 | 4.8 | 3.5 min |
| Ex. 37 | 96.5 DMT + 3.5 BE (4-o) | 221 | 182 | 39 | 5.0 | 3.25 min |
| Ex. 38 | 95 DMT + 5 BE (4-o) | 216 | 177 | 39 | 4.9 | 3.25 min |
| Ex. 24 | 127.5 OBT + 17.6 BE (3) | 225 | 186 | 39 | 7.2 | 3.25 min. |
| Ex. 25 | 250.8 OBT + 15.2 BE (4-p) | 225 | 181 | 44 | 5.0 | 3.75 min. |
| Ex. 27 | 250.8 OBT + 43.3 BE (4-p) | 223 | 186 | 47 | 6.0 | 3.75 |

(1) Measurements in air atmosphere, at heating rate of 8° C./min to 260° C. and then cooling rate of 4° C./min. 30 mg weighed in.
(2) Temperature of the peak maxima.
(3) Time from beginning to end of crystallization at constant cooling rate of 4° C./min.
BE (3) = Bisester of Structural Formula A3
BE (4-p) = Bisester of Structural Formula A4 with para substitution of xylylene radical and with the $$-\overset{O}{\underset{\|}{C}}-OR''$$ group in the para position BE (4-o) = Bisester of Structural Formula A4 with para substitution of xylylene radical and with the $$-\overset{O}{\underset{\|}{C}}-OR''$$ group in the ortho position.

OBT = oligomeric butylene terephthalate

TABLE 5

Hydrolysis resistance of the brominous linear copolyesters of the invention based on butanediol, DMT and bisesters (BE) of Structural Formulas A3 or A4 in comparison with PTMT, when pressed plates 1 mm thick are immersed in water, sulfuric acid or soda lye.

| Polyester of Ex. | Dicarb. Acid comp. (1) (numbers = mole-%) | Halogen content of polyester % Br | Halogen content of polyester % Cl | Hydrolysis conditions (2) | Reduced specific gravity after 0 days | Reduced specific gravity after 14 days | Reduced specific gravity after 28 days |
|---|---|---|---|---|---|---|---|
| Comp. Ex. 28 PTMT | 100 DMT | 0 | 0 | Water, 80° C. | 1.54 | 1.12 | 0.76 |
| | 100 DMT | 0 | 0 | H₂SO₄, 50° C. | 1.54 | 1.24 | 1.12 |
| | 100 DMT | 0 | 0 | NaOH, 50° C. | 1.54 | 1.18 | 1.06 |
| Ex. 21 | 95 DMT + 5BE(3) | 6.26 | 0 | Water, 80° C. | 0.94 | 0.85 | 0.80 |
| | 95 DMT + 5BE(3) | 6.26 | 0 | H₂SO₄, 50° C. | 0.94 | 0.90 | 0.82 |
| | 95 DMT + 5BE(3) | 6.26 | 0 | NaOH, 50° C. | 0.94 | 0.92 | 0.97 |
| Ex. 22 | 95 DMT + 5BE(4) | 6.07 | 0.3 | Water, 80° C. | 0.96 | 0.84 | 0.78 |
| | 95 DMT + 5BE(4) | 6.07 | 0.3 | H₂SO₄, 50° C. | 0.96 | 0.92 | 0.94 |
| | 95 DMT + 5BE(4) | 6.07 | 0.3 | NaOH, 50° C. | 0.96 | 0.92 | 0.90 |
| Ex. 23 | 96.5 DMT + 3.5BE(4) | 4.40 | 0.2 | Water, 80° C. | 1.35 | 1.22 | 1.16 |
| | 96.5 DMT + 3.5BE(4) | 4.40 | 0.2 | H₂SO₄, 50° C. | 1.35 | 1.24 | 1.26 |
| | 96.5 DMT + 3.5BE(4) | 4.40 | 0.2 | NaOH, 50° C. | 1.35 | 1.24 | 1.19 |

(FOOTNOTES:)
(1) BE(3) and BE(4) represent bisesters of Structural Formulas A3 and A4 respectively.
(2) 30 wt.-% aqueous sulfuric acid; 10 wt.-% aqueous caustic soda solution.
(3) Reduced specific gravity in a mixture of phenol and o-dichlorobenzene at 25° C., 1% solution.

Another aspect of the invention relates to bis-(carbalkoxybenzyl) ethers of halogenated bisphenols (Formula B1) and the preparation thereof.

Compounds having a plurality of functional groups bound to benzene nuclei have interesting characteristics for a number of applications.

Due to ether groups and, additionally, ester groups, such substances have polar groupings which are capable of changing the properties of the aromatic moiety. If the aromatic moieties additionally carry halogen atoms, suitability as fire-retardant agents for plastics can be speculated.

The subject matter of the present invention is bis(carbalkoxybenzyl) ethers of halogenated bisphenols of the formula

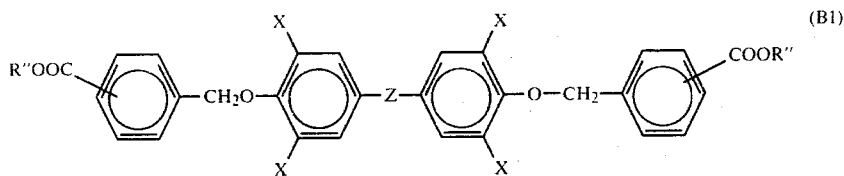

(B1)

wherein X represents bromine, chlorine or hydrogen, R" alkyl of 1 to 6 carbon atoms (the R"'s can be alike or different) and Z the groups

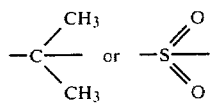

The four substitutents X can preferably be four bromine substituents, four chlorine substituents or four hydrogen substituents; however, the substances obtainable by the chlorobromination of bisphenol A, containing both chlorine and bromine atoms can also be substituents, those having a predominant number of bromine atoms being preferred.

Among the alkyl groups, those having 1 to 4 carbon atoms are preferred.

The new compounds are obtainable by the reaction of the bisphenols with alkali hydroxide and the isomeric chloromethylbenzoic acid alkyl esters, the reaction time being short and the yields being very high.

Additional subject matter of the invention, therefore, is a method of preparing the compounds of Formula B1, which is characterized in that tetrahalogenbisphenol A or tetrahalogendihydroxydiphenylsulfone, together with a sufficient amount of alkali hydroxide to form phenolate, is reacted in solution, at 40° to 150° C., with p-, m- or o-chloromethylbenzoic acid alkyl ester.

The preferred solvents are those in which sodium hydroxide, as well as the bisphenols or their phenolates, can be dissolved to a sufficient extent. Such solvents are to have boiling points above 90°, and generally above 100° C., preferably in mixture with water. Such solvents are especially ethylene glycol monomethyl ether (hereinafter called methyl glycol), and also dioxane, methylisobutylketone, methylethylketone, and others.

The amount of the water in these solvents is not critical, and, depending on the solubility of the substances to be dissolved, is as much as 65%, and is preferably up to 25%.

Sodium hydroxide is preferred as the alkali hydroxide, but potassium hydroxide and other hydroxides can also be used. The hydroxides can be added to the reaction mixture in the form of an aqueous solution. It is desirable to use amounts of alkali hydroxide which are equivalent to the bisphenol, since an excess results in secondary reactions with the chloromethyl benzoic acid ester.

The temperature in the reaction is generally 40° to 150° C., preferably 60° to 130° C., a temperature suitable for the preparation of the phenolates being best maintained between room temperatures and about 50° C. at the beginning. For the completion of the reaction, temperatures above 70° C., up to the boiling point of the solvent, are desirable.

The substances prepared precipitate in good purity either in the course of the reaction or when the mixture cools. Additional refinement is possible by washing with water until they are chloride-free or by recrystallization from a great variety of solvents.

The substances of the invention have comparatively high melting points up to over 250° C., especially in the case of the halogen aromatics of symmetrical structure, which is unusual in substances having a plurality of ether bonds and ester bonds.

Furthermore, the substances have a decidedly elongated molecular structure, which is particularly pronounced in the case of the derivatives of p-chloromethylbenzoic acid ester.

These characteristics have proven especially valuable for their use as fire-retardant agents.

The fabrication of plastics of all kinds containing these fire-retardants has proven to be greatly facilitated, because at the fabricating temperatures no decomposition of the substances of the invention has ever been observed.

The plastics equipped with the substances of the invention as fire-retardants have surprisingly shown virtually no sweating or chalking out of the fire-retardant when the plastics are exposed to heat for long periods.

In numerous groups of plastics, the addition of the substances of the invention results in a reduction of inflammability and the development of largely self-extinguishing properties. This is the case, for example, with polyolefins such as polyethylene and polypropylene, with polyesters such as polyethylene terephthalates and polybutylene terephthalates, and also with unsaturated polyesters, with polystryene and styrene copolymers, with polycarbonates, and others.

The amounts to be added will generally range from 2 to 20 weight-percent, the addition of antimony compounds such as antimony trioxide intensifying the effect.

The substances of the invention can furthermore serve as organic intermediates, and numerous reactions are possible, both on the basis of the ester group and on that of the halogen atoms.

EXAMPLE 39

Preparation of tetrabromobisphenol-A-bis(4-carbomethoxybenzyl) ether

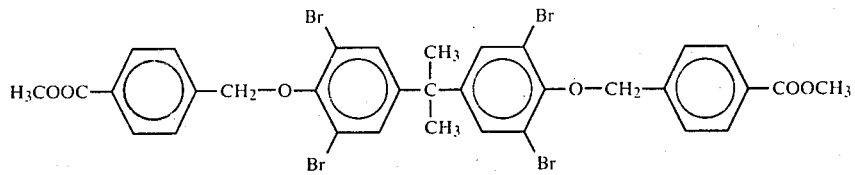

3.5 liters of ethylene glycol monomethyl ether (boiling point 122°–126° C.), hereinafter referred to as "methyl glycol" were combined with 816 g (1.5 moles) of tetrabromobisphenol A in a 6-liter three-necked flask provided with reflux condenser, stirrer and thermometer, and a solution of 120 g (3 moles) of sodium hydroxide in 120 ml of water was added, with stirring, and with self-heating. A clear solution of the sodium salt of the bisphenol is obtained, into which 554 g (3 moles) of p-chloromethylbenzoic acid methyl ester was stirred at about 40° C. The reaction mixture was then refluxed for 2 hours, with stirring. Beginning at an internal temperature of about 80° C., the mixture became turbid due to the segregation of sodium chloride.

At the end of the 2-hour refluxing period the mixture was cooled to room temperature, whereupon the bisether-bisester of the above formula separated in colorless crystals. It was suction filtered, washed with some cold methyl glycol, stirred up in water to remove sodium chloride, and then suction filtered again and re-washed with water until the filtrate was free of chloride. The product after drying amounted to 1160 g, corresponding to a yield of 92%, and the melting point was 155°–158.5° C. 15 grams of the substance, recrystallized from 45 ml of boiling xylene, yielded a crystallizate having a melting point of 157.5°–160° C.

Elemental Analysis: $C_{33}H_{28}Br_4O_6$ (840.23)

Calculated: C 47.17%, H 3.36%, Br 38.04%, O 11.42% Found: C 47.15%, H 3.42%, Br 37.89%, O 11.25%.

EXAMPLE 40

Preparation of tetrachlorobisphenol-A-bis(4-carbomethoxybenzyl) ether

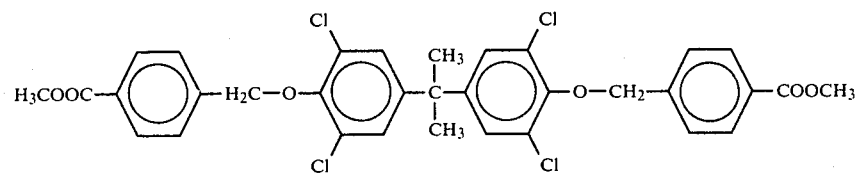

In a 2-liter three-necked flask equipped as in Example 39, the following were reacted by the procedure described therein:

800 ml of virtually water-free methyl glycol,
32 g (0.8 moles) of sodium hydroxide, dissolved in 40 ml of water,
146.4 g (0.4 mole) of tetrachlorobisphenol A, and
147.7 g (0.8 mole) of p-chloromethylbenzoic acid methyl ester.

At about 110° C., a colorless precipitate settled out of the previously clear reaction mixture, the amount increasing with the progress of the reaction. The mixture was refluxed for 1½ hours, then cooled, and the undissolved substance was removed by suction filtration. To remove sodium chloride, the filter cake was suspended in water, again suction filtered, and washed free of chloride ions. The product, still moist with water, was re-washed with methanol and dried in a circulating air drying oven at about 80° to 90° C.

228 g of colorless bisether-bisester melting at 152°–158° C. was obtained, corresponding to an 86.1% yield.

When recrystallized from acetic ester in a ratio of 1:9, the melting point was 159°–161.5° C.

Elemental Analysis: $C_{33}H_{28}Cl_4O_6$ (662.40)

Calculated: C 59.84%, H 4.26%, Cl 21.41%, O 14.49%. Found: C 59.91%, H 4.32%, Cl 21.50%, O 14.31%.

EXAMPLE 41

Preparation of tetrabromo-4,4'-dihydroxydiphenylsulfone-bis(4-carbomethoxybenzyl) ether

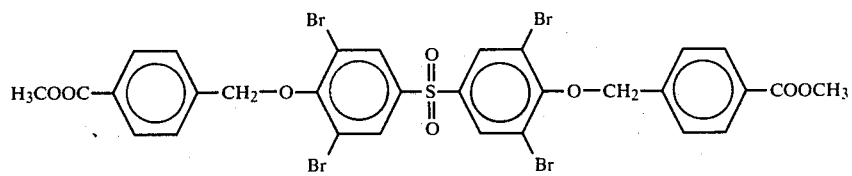

410 g (0.725 mole) of tetrabromo-4,4'-dihydroxydiphenylsulfone, 58 g (1.45 moles) of sodium hydroxide in 60 ml of water, and 268 g (1.45 moles) of p-chloromethylbenzoic acid methyl ester were reacted in 2 liters of methyl glycol (B.P. 117°–222° C.) in a four-liter three-necked flask by the procedure of Example 39, the mixture being refluxed, with stirring, for 1½ hours. The reaction started up 10 minutes after the boiling point was reached, and the contents of the flask gradually thickened due to the substance being precipitated. Then the mixture was suction filtered at room temperature and further processed as described above.

Yield after drying: 561 g (89.6% of the theory), with a melting point of 233°–238° C. A specimen was recrystallized twice from the dioxane in a ratio of 1:10; the melting point was then 238°–241° C.

Elemental Analysis: $C_{30}H_{22}Br_4O_8S$ (862.22)

Calculated: C 41.79%, H 2.57%, Br 37.07%, O 14.85%, S 3.72%. Found: C 42.01%, H 2.66%, Br 36.94%, O 14.72%, S 3.88%.

EXAMPLE 42

Preparation of 4,4'-dihydroxydiphenylsulfonebis(4-carbomethoxybenzyl) ether

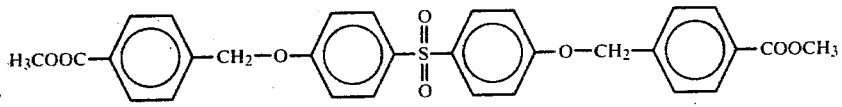

In the same manner as described in Example 41, we reacted the following in a two-liter reaction vessel:
1000 ml of methyl glycol, B.P. 122°–126° C.
125.2 g (0.5 mole) of 4,4'-sulfonyldiphenol,
56 g (1 mole) of potassium hydroxide in 60 ml of water and 184.6 g (1 mole) of p-chloromethylbenzoic acid methyl ester.

After 1½ hours of refluxing, during which potassium chloride precipitated beginning at an internal temperature of 80° C., the mixture was cooled down to 0° C. The crystallized solids were suction filtered, washed free of potassium chloride with water, and dried.

Yield: 227 g (83% of the theory) of M.P. 145°–155° C. This, when recrystallized from dioxane in a ratio of 1:5, yields the pure substance with a melting point of 161°–163° C.

Elemental Analysis: $C_{30}H_{26}O_8S$ (546.6)
Calculated: C 65.92%, H 4.79%, O 23.42%, S 5.87%. Found: C 65.77%, H 4.72%, O 23.54%, S 5.95%.

EXAMPLE 43

Preparation of tetrabromobisphenol-A-bis(4-carboethoxybenzyl) ether.

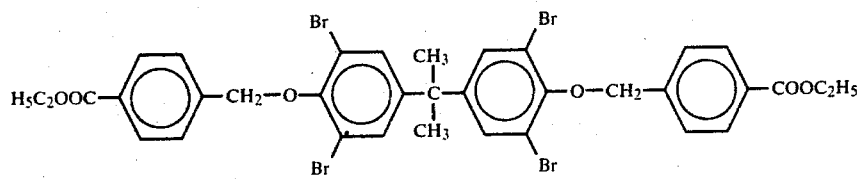

By the procedure of Example 39, the above ethyl ester was synthesized in a two-liter flask from 900 ml of methyl glycol (B.P. 117°–122° C.), 163.2 g (0.3 mole) of tetrabromobisphenol A, 24 g (0.6 mole) of sodium hydroxide in 24 ml of water, and 238.5 g (0.6 mole) of p-chloromethylbenzoic acid ethyl ester, the reaction mixture having been refluxed for 1½ hours. Sodium chloride formed beginning at an internal temperature of 90° C. This ester did not crystallize completely out of the reaction mixture until the temperature was lowered to −15° C. to −20° C.

The yield was 241 g (92% of the theory), M.P. 117–123 degrees C. When recrystallized from benzine (B.P. 80°–100° C.) in a ratio of 1:15, the melting point was 121°–123° C.

Elemental Analysis: $C_{35}H_{32}Br_4O_6$ (868.28)
Calculated: C 48.42%, H 3.71%, Br 36.81%, O 11.06%. Found: C 48.64%, H 3.66%, Br 36.95%, O 11.14%.

EXAMPLE 44

Tetrabromobisphenol-A-bis(4-carbobutoxybenzyl) ether.

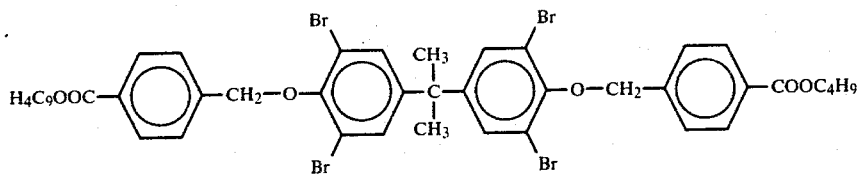

In the manner described in Example 39, we reacted the following mixture in a two-liter three-necked flask:
800 ml of methyl glycol (B.P. 117°–122° C.,
163.2 g (0.3 mole) of tetrabromobisphenol A
24 g (0.6 mole) of sodium hydroxide in 24 ml of water
136 g (0.6 mole) of p-chloromethyl-(benzoic acid-n-butyl ester).

The mixture was refluxed, with stirring, for 1½ hours, and then it was cooled to −20° C. overnight for crystallization; then it was processed as in Example 39.

Yield: 228 g (82% of the theory), M.P. 80°–89° C. Upon recrystallization from n-butanol in a ratio of 1:30, colorless needles, M.P. 91°–93.5° C.

Elemental Analysis: $C_{39}H_{40}Br_4O_6$ (924.4)
Calculated: C 50.67%, H 4.36%, Br 34.58%, O 10.38%. Found: C 50.82%, H 4.25%, Br 34.71%, O 10.44%.

EXAMPLE 45

Preparation of tetrabromobisphenol-A-bis(3-carbomethoxybenzyl) ether.

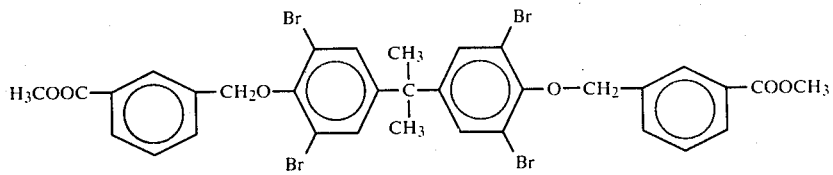

The following were reacted by the method of the invention as described above:

900 ml of methyl glycol (B.P. 122°–126° C.),
217.6 g (0.4 mole) of tetrabromobisphenol A
32 g (0.8 mole) of sodium hydroxide in 40 ml of water
147.4 g (0.8 mole) of m-chloromethylbenzoic acid methyl ester.

The segregation of sodium chloride began at about 85° C., while the bisether-biester formed during 1½ hours of refluxing remained in solution. It was precipitated by cooling to −20° C., and isolated as described.

Yield: 245 g (73% of the theory, M.P. 101°–108° C. Upon refinement by recrystallization from benzine (80°–100° C.) in a ratio of 1:40, the melting point became 116°–119° C.

Elemental Analysis: $C_{33}H_{28}Br_4O_6$ (840.23)
Calculated: C 47.17%, H 3.36%, Br 38.04%, O 11.42%. Found: C 47.31%, H 3.24%, Br 38.19%, O 11.56%.

Another aspect of the invention concerns the halogenated bis-(carbalkoxyphenoxymethyl)-benzenes referred to previously as halogenated xylylene-bis-(carbalkoxyphenyl) ethers, of Formula G2, and the preparation thereof.

Compounds having a plurality of functional groups bound to the benzene nucleus have interesting properties for a number of applications.

Due to the ether groups and, additionally, ester groups, such substances have polar groupings which are capable of altering the overall characteristics of the aromatic moiety. If the aromatic moieties additionally bear halogen atoms, suitability as fire-retardant agents for plastics is to be expected.

The subject matter of the present invention is bis(carbalkoxyphenoxymethyl)-benzenes of the formula

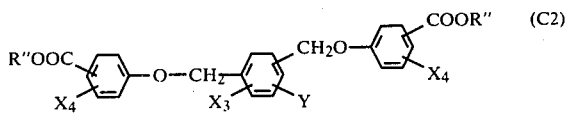

(C2)

wherein X represents bromine, chlorine or hydrogen, Y bromine or hydrogen, and R" alkyl with 1 to 6 carbon atoms. The R"'s can be alike or different.

The four selectable substituents on the central nucleus can be preferably four bromine atoms, in which case both the three substituents X and the substituent Y represent bromine. Also preferred are four hydrogen substituents and four substituents consisting partially of bromine and partially of chlorine, high proportions of 2.8 to 3.9 bromine and 1.2 to 0.1 chlorine also being preferred substituents. It is also possible, however, for one to three bromine substituents or also up to three chlorine substituents to be present in addition to hydrogen. The substituents of the two lateral aromatic nuclei are preferably either four hydrogens, or two halogens and two hydrogens, or four halogens; of the halogens, bromine is again preferred, or else a predominant proportion of bromine amounting to, say, 70 to 99 mole-%, especially from 85 mole-% up, plus chlorine. Of the alkyl groups, those having 1 to 4 carbon atoms are preferred.

The new compounds are easily obtainable with short reaction times and very high yields by the reaction of the isomeric bis-(chloromethyl)-benzenes or bis-(bromomethyl)-benzenes halogenated in the nucleus, with alkali hydroxide and the isomeric hydroxybenzoic acid alkyl esters.

Additional subject matter of the invention, therefore, is a method of preparing the compounds of Formula C2, which is characterized in that p-, m- or o-bis-(halogen-methyl)-benzenes, together with an amount of alkali hydroxide sufficient for the formation of phenolate, are reacted with p-, m- or o-hydroxybenzoic acid alkyl esters in solution at 40° to 150° C.

As solvents, those are preferred in which sodium hydroxide can be dissolved to a sufficient extent, as well as the hydroxyesters or their phenolates. Such solvents are to have boiling points above 90°, generally above 100° C., preferably in mixture with water. Such solvents are especially ethylene glycol monomethyl ether, and also dioxane, methylisobutylketone, methylethylketone, and others.

The amount of the water in these solvents is not critical and can amount to as much as 65%, preferably up to 25%, depending on the solubility of the substances to be dissolved.

Sodium hydroxide is preferred as the alkali hydroxide, although potassium hydroxide and other hydroxides can also be used. The hydroxides can be added in the form of an aqueous solution to the reaction mixture. It is desirable to use amounts of alkali hydroxide which are equivalent to the phenolic groups, since any excess results in undesirable reactions with the chloromethyl groups.

The temperature in the reaction will generally be 40° to 150° C., preferably 60° to 130° C., a temperature suitable for the preparation of the phenolate, between room temperature and about 50° C., being best maintained at the beginning. For the completion of the reaction, temperatures above 70° C. and up to the boiling point of the solvent are desirable.

The substances prepared precipitate in good purity from the solvent at the boiling temperature or upon the cooling of the reacted mixture. Further refinement is possible by washing with water until they are free of chloride, or by recrystallization from a wide variety of solvents.

The substances of the invention have comparatively high melting points ranging from over 160° C. to over 250° C., which is unusual in the case of substances having a plurality of ether bonds and ester bonds.

Furthermore, the substances have a decidedly elongated molecular structure, which is particularly pronounced in the cases of the derivatives of p-chloromethylbenzoic acid esters.

These properties have proven especially valuable for the use of these substances as fire-retardants.

The working of plastics of all kinds with contents of these fire-retardants, especially thermoplastic fabrication in an extruding machine, has proven to be greatly facilitated, since no decomposition of the substances of the invention has yet been observed at the processing temperatures.

The plastics treated with the substances of the invention as fire-retardants surprisingly undergo virtually no chalking-out or bleeding when the plastics are exposed to heat over long periods.

The addition of the substances of the invention results, in the case of numerous groups of plastics, in a reduction of inflammability and the development of largely self-extinguishing properties; this is the case, for example, with polyolefins such as polyethylene and polypropylene, with polyesters such as polyethyleneterephthalates and polybutyleneterephthalates, and with unsaturated polyesters, with polystyrene and styrene copolymers, with polycarbonates, and others.

The amounts added will generally range from 2 to 20%, by weight, the addition of antimony compounds, such as antimony trioxide, intensifying the effect.

The substances of the invention can furthermore serve as organic intermediates, numerous reactions being possible both on the basis of the ester group and on the basis of the halogen atoms.

EXAMPLE 46

Preparation of 1,4-bis-(p-carbomethoxyphenoxymethyl)-2,3,5,6-tetrabromobenzene

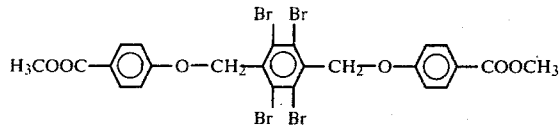

In a six-liter flask equipped with stirrer, reflux condenser and thermometer, 608.6 g (4 moles) of 4-hydroxybenzoic acid methyl ester was suspended in 3.5 liters of methyl glycol, and by the addition of 160 g (4 moles) of sodium hydroxide in 160 ml of water was transformed to a solution of the phenolate. Then, at about 35°–40° C., with stirring, 981.3 g (2 moles) of 1,4-bis-(chloromethyl)-2,3,5,6-tetrabromobenzene was put in, and the reaction mixture was raised steadily to the boiling temperature, with stirring. After an internal temperature of about 90° C. was reached, reaction started, with the formation of a colorless, voluminous precipitate. The reaction mixture, after becoming increasingly thick, became thinner again at the boiling temperature. It was refluxed for 1.5 hours, then cooled down to room temperature; the precipitate was suction filtered and washed free of sodium chloride with water, and dried.

We obtained 1276 g, corresponding to an 88.3% yield, of ester of the above structure, with a melting point of 263°–271° C. 5 grams, when recrystallized from 250 ml of xylene, yielded the pure substance melting at 272°–275° C.

Elemental analysis: $C_{24}H_{18}Br_4O_6$ (722.05)

Calculated: C 39.92%, H 2.51%, Br 44.27%, O 13.30% Found: C 40.21%, H 2.66%, Br 43.98%, O 13.19%.

EXAMPLE 47

Preparation of 1,3-bis-(p-carbomethoxy-phenoxymethyl)-2,4,5,6-tetrahalogenbenzene

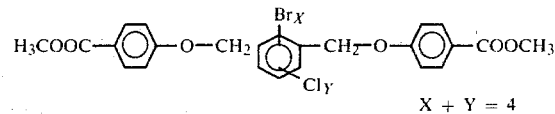

$X + Y = 4$

In a manner similar to Example 46, the following were reacted in a 250 ml three-necked flask:

200 ml of methyl glycol (B.P. 122°–126° C.), 30.4 g (0.2 mole) of 4-hydroxybenzoic acid methyl ester 8 g (0.2 mole) of sodium hydroxide in 8 ml of water 49 g (0.1 mole) of 1,3-bis-(chloromethyl)-2,4,5,6-tetrahalogenbenzene.

The 1,3-bis-(chloromethyl)-tetrahalogenbenzene had been obtained by side-chain chlorination from tetrabromo-m-xylene, and contained bromine and some chlorine in the nucleus due to chlorine-bromine exchange.

The mixture was refluxed with stirring for 1½ hours, sodium chloride precipitating, while the bisether-bisester of the above formula remained in solution at boiling heat. When the mixture cooled, the target product crystallized out beginning at an internal temperature of 100° C.

After room temperature had been reached, the product was suction filtered, washed free of sodium chloride with water, and the colorless crystallizate was dried.

The yield was 61 g, corresponding to 84% of the theoretically possible amount, melting at 167°–174° C. After recrystallization from methoxyethyl chloride, the melting point was 174°–176° C.

Elemental Analysis: $C_{24}H_{18}Br_{3.5}Cl_{0.5}O_6$ (699.82)

Calculated: C 41.18%, H 2.59%, Br 39.97%, Cl 2.53%, O 13.72%, Found: C 41.31%, H 2.54%, Br 39.90%, Cl 2.60%, O 13.49%.

EXAMPLE 48

Preparation of 1,2-bis-(p-carbomethoxyphenoxymethyl)-3,4,5,6-tetrahalogenbenzene

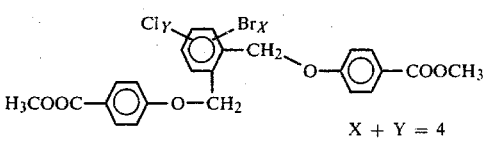

$X + Y = 4$

As described above, the following were reacted for 1½ hours, with stirring, at the boiling temperature of the mixture, in a 500-ml flask:

350 ml of methyl glycol (B.P. 122°–126° C.)

30.43 g (0.2 mole) of 4-hydroxybenzoic acid methyl ester 8 g (0.2 mole) of sodium hydroxide in 8 ml of water, 49 g (0.1 mole) of 1,2-bis-(chloromethyl)-3,4,5,6-tetrahalogenbenzene.

The reaction started up at about 50° C., and the bisester-bisether precipitated as a colorless substance. It was isolated as in the previous examples, and worked up. The yield was 57.3 g (79.5% of the theory) melting at 199° to 204° C. Recrystallization from methyl glycol in a ratio of 1:24 yielded a pure crystallizate melting at 205°–207° C.

Elemental Analysis: $C_{24}H_{18}Br_{3.1}Cl_{0.9}O_6$ (682)
Calculated: C 42.26%, H 2.66%, Br 36.32%, Cl 4.68%, O 14.07%, Found: C 42.49%, H 2.71%, Br 36.14%, Cl 4.81%, O 13.95%.

EXAMPLE 49

Preparation of 1,4-bis-(p-carbomethoxy-phenoxy-methyl)-benzene

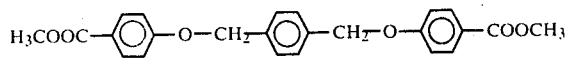

In a 500 ml flask, the following quantities and substances were reacted as in Example 46:
300 ml of methyl glycol (B.P. 122°–126° C.),
60.9 g (0.4 mole) of 4-hydroxybenzoic acid methyl ester
16 g (0.4 mole) of sodium hydroxide in 16 ml of water
35 g (0.2 mole) of d,d'-p-xylylenedichloride.

This reaction mixture was refluxed, with stirring, for two hours. Beginning at 60° C. internal. temperature, a clear solution was obtained, and at about 100° C. the substance of the above formula plus sodium chloride began to precipitate as a colorless mass.

After cooling to room temperature, the mixture was suction filtered, washed free of sodium chloride with water, and the bisether-bisester was dried.

Yield: 72.5 g, corresponding to 89% of the theory, M.P. 190°–195° C. 10 g of this was recrystallized twice from 100 ml of xylene and yielded the pure substance melting at 191.5°–192.5° C.

Elemental Analysis: $C_{24}H_{22}O_6$ (406.44)
Calculated: C 70.93%, H 5.46%, O 23.62%, Found: C 71.08%, H 5.61%, O 23.57%.

EXAMPLE 50

Preparation of 1,4-bis-(p-carbethoxy-phenoxymethyl)-2,3,5,6-tetrachlorobenzene

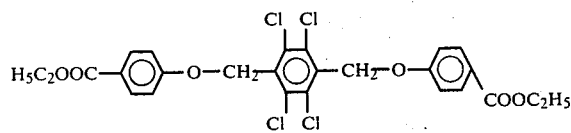

By the procedure of Example 46, 2 liters of methyl glycol, 80 g (2 moles) of sodium hydroxide in 80 ml of water, 332.3 g (2 moles) of 4-hydroxybenzoic acid ethyl ester and 313 g (1 mole) of 1,4-bis-(chloromethyl)-2,3,5,6-tetrachlorobenzene were reacted in a four-liter reaction vessel, the reaction beginning vigorously at 100° C., and the product precipitated. The mixture was refluxed for one hour, and then cooled down to room temperature and worked up as previously described.

The yield was 488 g (85.4% of the theory), the melting point 195° to 203° C. By recrystallization from xylene in a 1:4 ratio, we obtained the pure substance melting at 203°–205° C.

Elemental Analysis: $C_{26}H_{22}Cl_4O_6$ (572.27)
Calculated: C 54.57%, H 3.87 %, Cl 24,78%, O 16.77%. Found: C 54.39%, H 3.82%, Cl 24.94%, O 16.86%.

EXAMPLE 51

Preparation of 1,4-bis-(p-carbomethoxyphenoxy-methyl)-2,3,5,6-tetrachlorobenzene The methyl ester corresponding to Example 50 was similarly obtained from 2 liters of methyl glycol (B.P. 122°–126° C.), 80 g (2 moles) of sodium hydroxide in 80 ml of water, 304.3 g (2 moles) of 4-hydroxybenzoicacid methyl ester, and 313 g (1 mole) of 1,4-bis-(chloromethyl)-2,3,5,6-tetrachlorobenzene.

The yield was 499 g (91.7% of the theory), melting at 242°–250° C. Upon recrystallization from xylene in a ratio of 1:30, the pure compound was obtained, melting at 250° to 253° C.

Elemental Analysis: $C_{24}H_{18}Cl_4O_6$ (544.22)
Calculated: C 52.97%, H 3.33%, Cl 26.06%, O 17.64%, Found: C53.14%, H 3.22%, Cl 25.89%, O 17.78%.

EXAMPLE 52

Preparation of 1,3-bis-(carbomethoxyphenoxymethyl)-2,4,5,6-tetrachlorobenzene

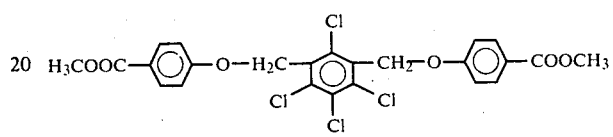

In a six-liter reaction vessel, 3 liters of methyl glycol (B.P. 117°–122° C.), 200 g (5 moles) of sodium hydroxide in 200 ml of water, 761 g (5 moles) of 4-hydroxybenzoicacid methyl ester and 782 g (2.5 moles) of 1,3-bis-(chloromethyl)-2,4,5,6-tetrachlorobenzene were reacted by the procedure of Example 46 and worked up.

The yield was 1195 g (88% of the theory) melting at 161° to 165° C. Upon recrystallization from methoxyethyl chloride in a ratio of 1:5, the pure substance is obtained, which melts at 165°–167° C.

Elemental Analysis: $C_{24}H_{18}Cl_4O_6$ (544.22)
Calculated: C 52.97%, H 3.33%, Cl 26.06%, O 17.64%, Found: C 52.87%, H 3.39%, Cl 26.27%, O 17.44%.

EXAMPLE 53

Preparation of 1,3-bis-(4-carbomethoxy-2,6-dichloro-phenoxymethyl)-2,4,5,6-tetrabromobenzene

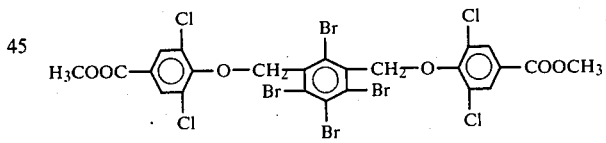

In a four-liter reaction vessel, 3 liters of methyl glycol (B.P. 122°–126° C.), 221 g (1 mole) of 3,5-dichloro-4-hydroxybenzoic acid methyl ester, 40 g (1 mole) of sodium hydroxide in 40 ml of water, and 289.8 g (0.5 mole) of 1,3-bis-(bromomethyl)-2,4,5,6-tetrabromobenzene were reacted and worked up in the manner described in Example 46.

The reaction started up at 95° C. with the formation of a voluminous, colorless precipitate. The reaction time was 1.5 hours, with stirring, at the refluxing temperature.

The yield was 362 g (84.2% of the theory) melting at 253°–258° C. 10 g, recrystallized from 300 ml of 1,2-dibromoethane, yielded the pure bisester-bisether of the above structure, melting at 266°–268° C.

Elemental Analysis: $C_{24}H_{14}Br_4Cl_4O_6$ (859.83)
Calculated: C 33.53%, H 1.64%, Br 37.17%, C 16.49%, O 11.17%, Found: C 33.68%, H 1.53%, Br 37.02%, Cl 16.60%, O 11.28%.

EXAMPLE 54

Preparation of 1,4-bis-(4-carbomethoxy-2,6-dibromo-phenoxymethyl)-2,3,5,6-tetrabromobenzene The following were reacted by the method of the invention as described in the foregoing examples:

600 ml of methyl glycol (B.P. 122°-126° CO., 37.2 g (0.12 mole) of 3,5-dibromo-4-hydroxybenzoic acid methyl ester, 4.8 g (0.12 mole) of sodium hydroxide in 5 ml of water, and 34.8 g (0.06 mole) of 1,4-bis-(bromomethyl)-2,3,5,6-tetrabromobenzene.

The reaction starts at about 70° to 75° C.; the refluxing time was 1½ hours. The target product precipitated beginning at an internal temperature of 110° C.

The yield was 52.5 g (84.2% of the theory) melting at 297°-301° C. 25 g of this, when recrystallized from 900 ml of 1,2-dibromoethane, yielded a pure crystallizate melting at 302°-304° C.

Elemental Analysis: $C_{24}H_{14}Br_8O_6$ (1,037.65)

Calculated: C 27.78%, H 1.36%, Br 61.61%, O 9.25%, Found: C 27.66%, H 1.29%, Br 61.80%, O 9.29%.

What is claimed is:

1. Bis-(carbalkoxy-benzyl)-ether of bisphenols of the formula wherein X represents bromine, chlorine or hydrogen, -R"- represents alkyl of 1 to 6 carbon atoms and Z represents the groups 2. Ether of claim 1, wherein X is bromine or chlorine.

3. Process of preparing an ether of claim 1 wherein X is halogen, wherein tetrahalogenbisphenol A or tetrahalogendihydroxy-diphenylsulfone, together with an amount of alkali hydroxide sufficient for the formation of the corresponding phenolate, is reacted in solution at 40° to 150° C. with p-, m- or o-chloromethylbenzoic acid alkyl esters.

4. Bis-(carbalkoxy-phenoxymethyl)-benzene of the formula wherein X represents bromine, chlorine or hydrogen, and Y represents bromine, chlorine or hydrogen, and R" represents alkyl of 1 to 6 carbon atoms.

5. Method of preparing the benzene compound of claim 4, wherein p-, m- or o-bis-(halogenmethyl)-benzene together with an amount of alkali hydroxide sufficient for the formation of the corresponding phenolate are reacted with p-, m- or o-hydroxybenzoic acid alkyl ester at 40° to 150° C.

6. Process of preparing ether of claim 1 wherein the corresponding bisphenol or the corresponding diphenyl sulfone, together with an amount of alkali hydroxide sufficient for the formation of the corresponding phenolate, is reacted in solution at 40° to 150° C. with p-, m- or o-chloromethylbenzoic acid alkyl esters.

* * * * *